(12) United States Patent
Priebe et al.

(10) Patent No.: US 7,745,468 B2
(45) Date of Patent: Jun. 29, 2010

(54) COMPOUNDS FOR TREATMENT OF CELL PROLIFERATIVE DISEASES

(75) Inventors: Waldemar Priebe, Houston, TX (US); Nicholas Donato, Sugarland, TX (US); Moshe Talpaz, Houston, TX (US); Slawomir Szymanski, Houston, TX (US); Izabela Fokt, Houston, TX (US); Alexander Levitzki, Jerusalem (IL)

(73) Assignee: Board of Regents, University of Texas Systems The, Austin, TX (US)

( * ) Notice: Subject to any disclaimer, the term of this patent is extended or adjusted under 35 U.S.C. 154(b) by 1259 days.

(21) Appl. No.: 11/010,834

(22) Filed: Dec. 13, 2004

(65) Prior Publication Data

US 2005/0277680 A1 Dec. 15, 2005

Related U.S. Application Data

(60) Provisional application No. 60/528,877, filed on Dec. 11, 2003.

(51) Int. Cl.
*A61K 31/44* (2006.01)
*C07D 213/57* (2006.01)

(52) U.S. Cl. ....................... 514/357; 546/330

(58) Field of Classification Search ................. 546/230, 546/337, 330; 514/357, 331
See application file for complete search history.

(56) References Cited

U.S. PATENT DOCUMENTS

| | | | | |
|---|---|---|---|---|
| 4,999,357 | A | 3/1991 | Gadras et al. | 514/277 |
| 5,196,446 | A | 3/1993 | Levitzki et al. | 514/415 |
| 5,700,822 | A | 12/1997 | Hirth et al. | 514/380 |
| 5,773,476 | A | 6/1998 | Chen et al. | 514/620 |
| 5,854,285 | A | 12/1998 | Sriram et al. | 514/514 |
| 5,981,569 | A | 11/1999 | App et al. | 514/419 |
| 6,194,453 | B1 | 2/2001 | Sriram et al. | 514/514 |
| 6,225,346 | B1 | 5/2001 | Tang et al. | 514/523 |
| 6,331,555 | B1 | 12/2001 | Hirth et al. | 514/378 |
| 6,420,338 | B1 | 7/2002 | Schneider et al. | 514/12 |
| 6,426,366 | B1 | 7/2002 | Novogrodsky et al. | 514/523 |
| 6,433,018 | B1 | 8/2002 | Siddiqui et al. | 514/619 |
| 6,555,702 | B2 | 4/2003 | Sriram et al. | 558/402 |
| 6,596,828 | B1 | 7/2003 | Kaito et al. | 526/164 |
| 6,596,878 | B2 | 7/2003 | Chen et al. | 548/371.7 |
| 2002/0045191 | A1 | 4/2002 | Schneider et al. | 435/7.1 |
| 2002/0115714 | A1 | 8/2002 | Sriram et al. | 514/514 |
| 2003/0013748 | A1 | 1/2003 | Novogrodsky et al. | 514/367 |
| 2003/0032596 | A1 | 2/2003 | Schneider et al. | 514/12 |
| 2007/0232668 | A1* | 10/2007 | Priebe et al. | 514/357 |

FOREIGN PATENT DOCUMENTS

| | | |
|---|---|---|
| DE | 2555789 A1 | 7/1977 |
| WO | WO 91/16305 | 10/1991 |
| WO | WO 95/14464 | 1/1995 |
| WO | WO 95/24190 | 9/1995 |
| WO | WO 98/06391 | 2/1998 |
| WO | WO 2005/058829 | 6/2005 |
| WO | WO 99/05109 A1 | 2/2009 |

OTHER PUBLICATIONS

1994:457456 Hcaplus Abstract, Journal of Heterocyclic Chemistry, 31, 329, pp. 329-331, "Reaction of Emaminonitriles with Isocyanates. Synthesis of New 2-Oxo and 6-oxopyrimadines", Cocco et. al.*
Hcaplus 1998:545399.*
Hcaplus 2005:246273.*
Levitzki, Alexander, "Tyrphostins: tyrosine kinase blockers as novel antiproliferative agents and dissectors of signal transduction", The FASEB Journal, vol. 6, Nov. 1992, pp. 3275-3282.*
Alas and Bonavida, "Inhibition of constitutive STAT3 activity sensitizes resistant non-Hodgkin's lymphoma and multiple myeloma to chemotherapeutic drug-mediated apoptosis," *Clin. Cancer Res.*, 9(1):316-26, 2003.
Alcon et al, "Activation of Tyrosine Kinase Pathway by Vanadate in Gallbladder Smooth Muscle," *Biochem. Pharmacol.*, 59:1077-1089, 2000.
Arbel et al., "Inhibitors that target protein kinases for the treatment of ovarian carcinoma," *Am. J. Obstet. Gynecol.*, 188(5):1283-90, 2003.
Bharti et al., "Curcumin (diferuloylmethane) inhibits constitutive and IL-6-inducible STAT3 phosphorylation in human multiple myeloma cells," *J. Immunol.*, 171(7):3863-3871, 2003.
Burdelya et al, "Combination therapy with AG-490 and interleukin 12 achieves greater antitumor effects than either agent alone," *Mol. Cancer Ther.*, 1(11):893-9, 2002.
Catlett-Falcone et al., "Constitutive activation of Stat3 signaling confers resistance to apoptosis in human U266 myeloma cells," *Immunity*, 10(1):105-15, 1999.
Constantin et al., "Tyrphostin AG490, a tyrosine kinase inhibitor, blocks actively induced experimental autoimmune encephalomyelitis," *Eur. J. Immunol.*, 28(11):3523-9, 1998.
De Vos et al., "JAK2 tyrosine kinase inhibitor tyrphostin AG490 down regulates the mitogen-activated protein kinase (MAPK) and signal trasducer and activator of transcription (STAT) pathways and induces apoptosis in myeloma cells," *Br. J. Haematol.* 109:823-828, 2000.
Gazit et al., "Tyrphostins. 2. Heterocyclic and alpha-substituted benzylidenomalononitrile tyrphostins as potent inhibitors of EG receptor and ErbB2/nue tyrosine kinases," *J. Med. Chem.*, 34(6):1896-1907, 1991.
Gazit, et al, "Tyrphostins I; synthesis and biological activity of protein tyrosine kinase inhibitors," *J. Med. Chem.*, 32:2344-2352, 1989.
Hallek et al., "Multiple myeloma: increasing evidence for a multistep transformation process," *Blood*, 91(1):3-21, 1998.
Hideshima et al., "NF-kappa B as a therapeutic target in multiple myeloma," *J. Biol. Chem.*, 277(19):16639-16647, 2002.
Jernberg-Wiklund et al, "Expression of myc-family genes in established human multiple myeloma cell lines: L-myc but not c-myc gene expression in the U-266 myeloma cell line," *Int. J. Cancer*, 51(1):116-123, 1992.

(Continued)

*Primary Examiner*—Janet L. Andres
*Assistant Examiner*—Binta M Robinson
(74) *Attorney, Agent, or Firm*—Fulbright & Jaworski LLP

(57) ABSTRACT

The present invention concerns compounds and their use to treat cell proliferative diseases such as cancer. Compounds of the present invention display significant potency as kinase inhibitors, cause the downregulation of c-myc, and inhibit the growth and survival of cancerous cell lines.

23 Claims, 9 Drawing Sheets

OTHER PUBLICATIONS

Kerr et al., "Of JAKs, STATs, blind watchmakers, jeeps and trains," *FEBS Lett.*, 546(1):1-5, 2003.

Kirken et al., "Tyrphostin AG0490 inhibits cytokine-mediated JAK3/STAT5a/b signal transduction and cellular proliferation of antigen-activated human T cells," *J.Leukoc. Biol.*, 65:891-899, 1999.

Kuehl et al., "Dysregulation of c-myc in multiple myeloma," *Curr. Top Microbial. Immunol.*, 224:277-282, 1997.

Levitzki et al., "Tyrosine phosphorylation is an obligator event in IL-2 secretion," *Biochem. Pharmacol.* 40:913-918, 1990.

Meydan et al, "Inhibition of acute lymphoblastic leukaemia by a Jak-2 inhibitor," *Nature* 379:645-648, 1996.

Renglin et al., "Miotic aberrations induced by carbaryl reflect tyrosine kinase inhibition with coincident up-regulation of serine/threonine protein phosphatase activity: implications for coordination of karyokinesis and cytokinesis," *Mutagenesis*. 14(3):327-334, 1999.

Selvanayagam et al., "Alternation and Abnormal Expression of the c-myc Oncogene in Human Multiple Myeloma," *Blood*, 71(0:30-35, 1988.

Verma et al., "Jak family of kinases in cancer," *Cancer Metastasis Rev.*, 22(4):423-434, 2003.

Volberg et al, "Disruption of Microtubules in Living Cells by Tyrphostin AG-1714," *Cell Motility and the Cytaskelton*, 45(3):223-234; 2000.

Wang et al., "JAK3, STAT, and MAPK signaling pathways as novel molecular target for the tyrphostin AG-490 regulation of IL-2-mediated T cell response," *J. Immunol*, 162:3897-3904, 1999.

"Design, Synthesis and Structure-Activity Relationships of Novel Jak2/STAT3 Signaling Inhibitors," AACR Abtract Later Breaking News, Feb. 1, 2006 (Abstract No. 06-LBA-8902-AACR).

Chen et al., "Human pancreatic adenocarcinoma: in vitro and in vivo morphology of a new tumor line established from ascites," *In Vitro*, 18(1):24-34, 1982.

Iwamaru et al., "A novel inhibitor of the STAT3 pathway induces apoptosis in malignant glioma cells both in vitro and in vivo," *Oncogene*, 26: 2435-44, 2007.

Lieber et al., "Establishment of a continuous tumor-cell line (panc-1) from a human carcinoma of the exocrine pancreas," *Int. J. Cancer*, 15(5):741-747, 1975.

Morgan et al., "Human cell line (colo 357) of metastatic pancreatic adenocarcinoma," *Int. J. Cancer*, 25(5):591-598, 1980.

Satyamoorthy et al., "Melanoma cell lines from different stages of progression and their biological and molecular analyses," *Melanoma Res.*, 7(Suppl.2):S35-S42, 1997.

Vezeridis et al., "In vivo selection of a highly metastatic cell line from a human pancreatic carcinoma in the nude mouse," *Cancer*, 69(8):2060-2063, 1992.

Vezeridis et al., "Heterogeneity of potential for hematogenous metastasis in a human pancreatic carcinoma," *J. Surg. Res.*, 48(1):51-55, 1990.

Yu and Jove, "The stats of cancer-new molecular targets come of age," *Nature Rev. Cancer*, 4(2):97-105, 2004.

Database CA, Accession No. 96215, 1999.
Database CA, Accession No. 446109, 1976.
Database CA, Accession No. 478235, 1990.
Database CA, Accession No. 584231, 1977.
Database Crossfire Beilstein, Accession No. 9145100.

European Supplementary Search Report, issued in PCT/US2004/041712, dated Oct. 10, 2008.

Tamiz et al., "Structure-Activity Relationship of N- (Phenylalkyl) cinnamides as Novel NR2B Subtype-Selective NMDA Receptor Antagonists," *J. of Medicinal Chemistry*, 42 (17): 3412-3420, 1999.

Farooki et al., "Tyrphostins disrupt stress fibers and cellular attachments in endothelial monolayers," *Exp. Cell. Res.*, 243 (1): 185-198, 1998.

Zlotnik et al., "Tyrphostins reduce chemotherapy-induced intestinal injury in mice: assessment by a biochemical assay," *Br. J. Cancer*, 92 (2): 294-297, 2005.

Office Action, issued in Chinese Application No. 200480037045.0, date of dispatch Jul. 24, 2009 (English Translation).

Burke et al., "Inhibition of constitutively active Stat3 suppresses growth of human ovarian and breast cancer cells," *Oncogene*, 20:7925-7934, 2001.

* cited by examiner

$C_{17}H_{14}BrN_3O$
Mol. Wt.: 356.217

$IC_{50} = \sim 1300$ nM

WP1130

$C_{19}H_{18}BrN_3O$
Mol. Wt.: 384.27

$IC_{50} = \sim 950$ nM

WP1129

$C_{18}H_{16}BrN_3O$
Mol. Wt.: 370.243

$IC_{50} = \sim 800$ nM

WP 1126

$C_{15}H_{16}BrN_3O_6$
Mol. Wt.: 414.21
C, 43.50; H, 3.89; Br, 19.29; N, 10.14; O, 23.18

WP 1119

$C_{21}H_{24}BrN_3O_6$
Mol. Wt.: 494.34
C, 51.02; H, 4.89; Br, 16.16;
N, 8.50; O, 19.42

WP 1127

$C_{23}H_{24}BrN_3O_{10}$
Mol. Wt.: 582.35
C, 47.44; H, 4.15; Br, 13.72; N, 7.22; O, 27.47

COMPOUNDS FOR TREATMENT OF CELL PROLIFERATIVE DISEASES

This application claims the benefit of U.S. Provisional Application Ser. No. 60/528,877 filed Dec. 11, 2003, the entire disclosure of which is specifically incorporated herein by reference.

BACKGROUND OF THE INVENTION

1. Field of the Invention

The present invention relates generally to the treatment of cell proliferative diseases such as cancer. More particularly, it concerns tyrphostin and tyrphostin-like compounds useful for the treatment of cell proliferative diseases such as cancer, methods of synthesis of these compounds, and methods of treatment employing these compounds.

2. Description of Related Art

AG490 is a kinase inhibitor that inhibits Jak2/Stat3 signaling. Targeted inhibition of the Jak/Stat pathway with AG490 inhibits tumor cell growth and increases sensitivity to apoptotic stimuli; thus, inhibitors of this pathway likely represent potential therapeutics for cancer therapy (Catlett-Falcone et al., 1999; Alas and Bonavida, 2003; Burdelya et al., 2002). Because IL-6 promotes survival and proliferation of certain cancerous cell lines through the phosphorylation of STAT3 (Bharti et al., Verma et al., Kerr et al.), kinase inhibitors similar to AG490 have potential as anti-cancer drugs.

AG490 is structurally classified as a tyrphostin. U.S. Pat. No. 6,596,828B2 and U.S. patent application 2003/0013748 describe compounds that have structural similarity with AG490.

Unfortunately, AG490 has limited activity in animal studies and must be used at high concentrations (~50 to 100 μM) to achieve inhibition of Jak2/Stat3 signaling and anti-tumor effects, and this low potency of AG490 is insufficient to warrant clinical investigation of this compound for the treatment of cancer (Burdelya et al., 2002; Meydan et al., 1996; Constantin et al., 1998). Thus a need exists for therapeutics that exhibit strong anti-proliferative effects through a similar mechanism at lower therapeutic concentrations.

SUMMARY OF THE INVENTION

The present invention overcomes limitations in the art by providing compounds that display improved pharmacological profiles (e.g., increased potency) when compared with AG490; these compounds block IL-6 mediated Stat3 activation at low concentrations (~1 μM) and rapidly suppress expression of the c-myc proto-oncogene, which is frequently overexpressed, rearranged, or mutated in many malignancies (Hallek et al., 1998; Selvanayagam et al., 1988; Jernberg-Wiklund et al., 1992; Kuehl et al., 1997). Additionally, compounds of the present invention also induce apoptosis in c-myc overexpressing tumor cells that parallels their c-myc downregulatory activity. The present invention involves compounds that have utility as antitumor and/or chemotherapeutic drugs, methods of synthesizing these compounds, and methods of using these compounds to treat patients with cancer.

One aspect of the present invention relates to a compound comprising the chemical formula:

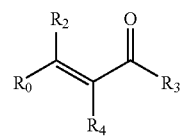

wherein $R_0$ is selected from the group consisting of $R_1$ and $R_1\text{-}Z_1\text{-}$; and wherein $Z_1$ is alkyl; and wherein $R_1$ is chosen from the group consisting of:

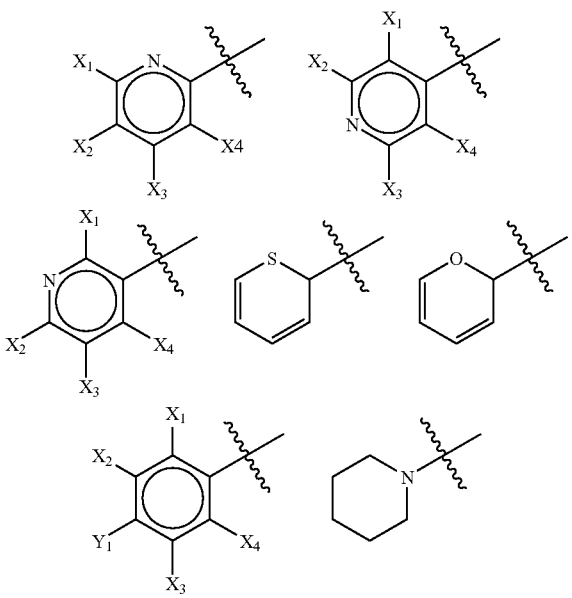

where $X_1$, $X_2$, $X_3$, and $X_4$, are each independently selected from the group consisting of hydrogen, halogen, alkyl, alkoxy, OH, trihalomethyl, and $NO_2$;

where $Y_1$ is selected from the group consisting of halogen and $O_2N$; and $R_2$ is selected from the group consisting of alkyl, alkenyl, alkynyl, alkoxy, alkylaryl, halogen, hydrogen, OH, $NO_2$, thioether, amine, SH, and $NH_2$;

$R_3$ is selected from the group consisting of:

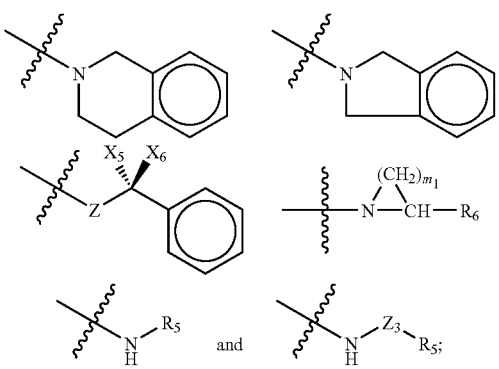

wherein $Z_3$ is alkyl; and wherein $m_1$=1, 2, 3, or 4; and where $R_4$ is chosen from the group consisting of: CN, substituted amine, $CH_2S$-alkyl, alkyl, and $CH_2N_3$;

where $R_5$ and $R_6$ are each independently chosen from the group consisting of:

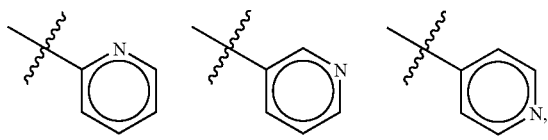

monosaccharide, monosaccharide derivative, polysaccharide, polysaccharide derivative, aryl, and alkylaryl;

where Z is selected from the group consisting of NH, S, and O, and where $X_5$ and $X_6$ are each independently chosen from the group consisting of hydrogen and lower alkyl.

In certain embodiments of the present invention, $R_4$ is CN. In certain embodiments, $R_1$ may be chosen from the group consisting of:

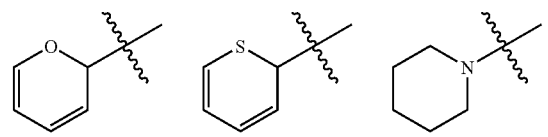

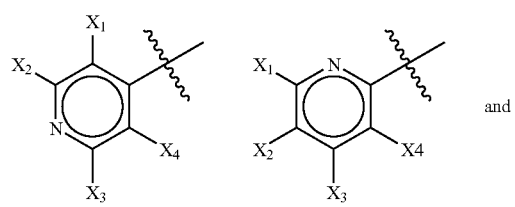

In more specific embodiments, $R_1$ is:

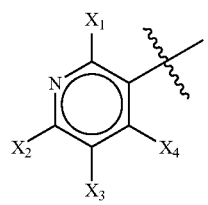

In certain embodiments, $X_1$ is a halogen such as Br.

$R_5$ may be chosen from the group consisting of an alkylaryl having the structure:

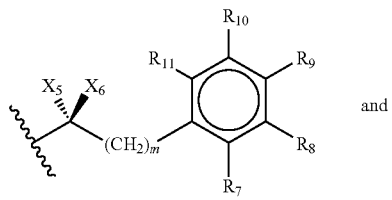

an aryl having the structure:

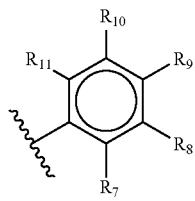

wherein m=0, 1, 2, 3, 4, 5, 6, or 7 and where $X_5$ and $X_6$ are each independently chosen from the group consisting of hydrogen and alkyl, and where $R_7$, $R_8$, $R_9$, $R_{10}$, and $R_{11}$, are each independently selected from the group consisting of hydrogen, halogen, alkyl, alkoxy, OH, trihalomethyl, and $NO_2$.

In more specific embodiments $R_5$ is an alkylaryl. $X_1$, $X_2$, $X_3$, and $X_4$ may be hydrogen. $Z_1$ may be a lower alkyl, and the lower alkyl may be —$(CH_2)_{m3}$—, wherein M3=0, 1, 2, 3, or 4.

$Z_3$ may be a lower alkyl, and the lower alkyl may be —$(CH_2)_{m4}$—, wherein M4=0, 1, 2, 3, or 4. $Y_1$ may be $O_2N$ or a halogen, such as Cl or Br.

In certain embodiments, $R_5$ is selected from the group consisting of:

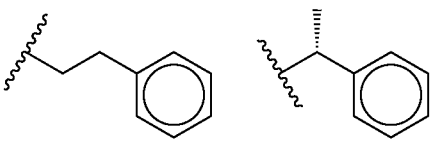

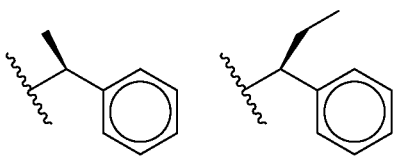

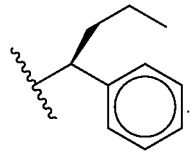

$R_2$ may be hydrogen. $Y_1$ may be selected from the group consisting of $O_2N$ and a halogen, such as Br or Cl.

Certain embodiments of the present invention relate to a compound having the formula:

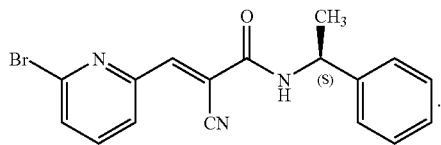

Certain embodiments of the present invention relate to a compound having the formula:

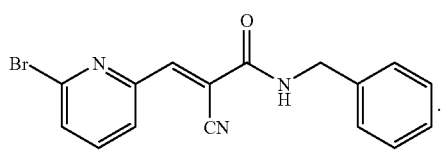

Certain embodiments of the present invention relate to a compound having the formula:

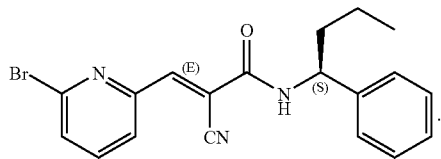

Certain embodiments of the present invention relate to a compound having the formula:

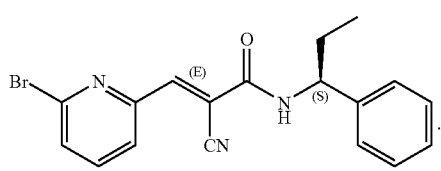

Certain embodiments of the present invention relate to a compound having the formula:

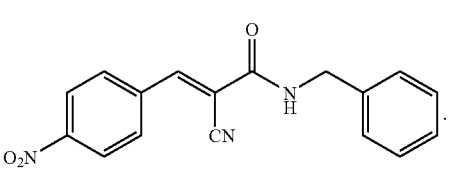

Certain embodiments of the present invention relate to a compound having the formula:

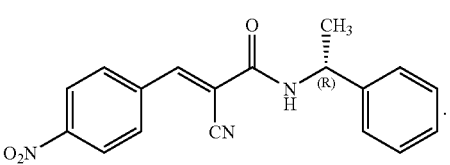

Certain embodiments of the present invention relate to a compound having the formula:

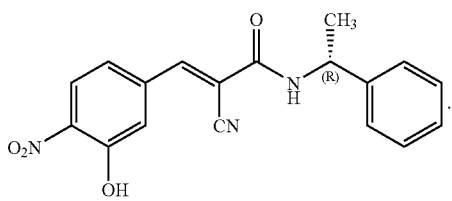

Certain embodiments of the present invention relate to a compound having the formula:

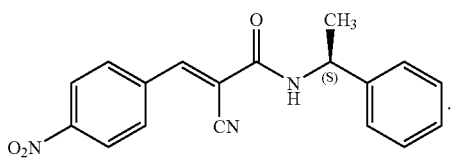

Certain embodiments of the present invention relate to a compound having the formula:

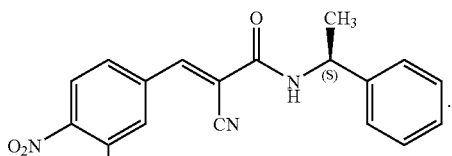

Certain embodiments of the present invention relate to a compound having the formula:

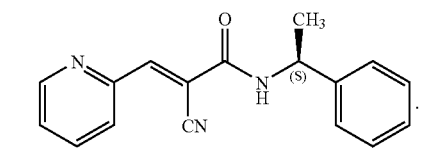

Certain embodiments of the present invention relate to a compound having the formula:

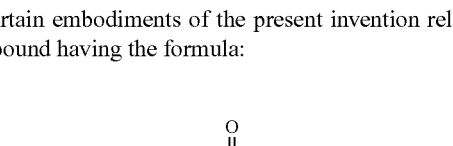

Certain embodiments of the present invention relate to a compound having the formula:

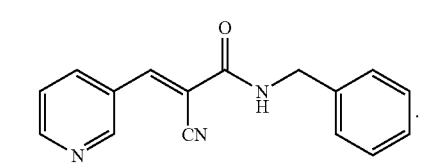

Certain embodiments of the present invention relate to a compound having the formula:

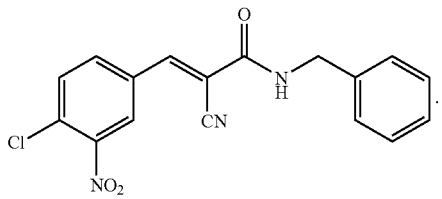

Another aspect of the present invention concerns a method of treating a cell proliferative disease comprising administering a therapeutically relevant amount of a first compound of the present invention to a subject. The subject may be a mammal, and the mammal may be a human. The first compound may be comprised in a pharmaceutically acceptable excipient, diluent, or vehicle. The cell proliferative disease may be cancer. The cancer may be melanoma, non-small cell lung, small cell lung, lung, hepatocarcinoma, retinoblastoma, astrocytoma, glioblastoma, leukemia, blood, brain, skin, eye, tongue, gum, neuroblastoma, head, neck, breast, pancreatic, renal, bone, testicular, ovarian, mesothelioma, cervical, gastrointestinal, lymphoma, colon, or bladder.

The cell proliferative disease may be rheumatiod arthritis, inflammatory bowel disease, osteoarthritis, leiomyomas, adenomas, lipomas, hemangiomas, fibromas, vascular occlusion, restenosis, artherosclerosis, a pre-neoplastic lesion, carcinoma in situ, oral hariy leukoplakia, or psoriasis.

In certain embodiments, stat3 activation is reduced in a cell of the subject. c-myc expression may be reduced in a cell of the subject. The first compound may be administered in combination with a therapeutically relevant amount of a second compound. The second compound may be an anti-cancer compound. The first compound may be administered in combination with a surgery, a radiation therapy, or a gene therapy.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A, Dose response relationships for compounds in MM-1 MM cells. The MM cells were incubated with the indicated concentration of AG or WP compound for 72 hours before cell growth and survival were estimated by MTT assay. Compounds AG1801, AG490, and WP1034 were effective in reducing the growth and survival of MM1 cells. FIG. 2B, Dose response relationships for compounds in OCI MM cells. Compounds AG1801, AG490, and WP1034 were effective in reducing the growth and survival of the OCI cells. FIG. 2C, Dose response relationships for compounds in U266 MM cells. Compounds AG1801, AG490, and WP1034 were effective in reducing the growth and survival of the U266 cells.

FIG. 3A, AG1801, WP1034, and WP1050 inhibited the growth and survival of MM1 cells and demonstrated increased potency compared to AG490. FIG. 3B, AG1801, WP1034, and WP1050 inhibited the growth and survival of OCI cells and demonstrated increased potency compared to AG490. FIG. 3C, AG1801, WP1034, and WP1050 inhibited the growth and survival of U266 cells and demonstrated increased potency compared to AG490.

DESCRIPTION OF ILLUSTRATIVE EMBODIMENTS

Figure 1:
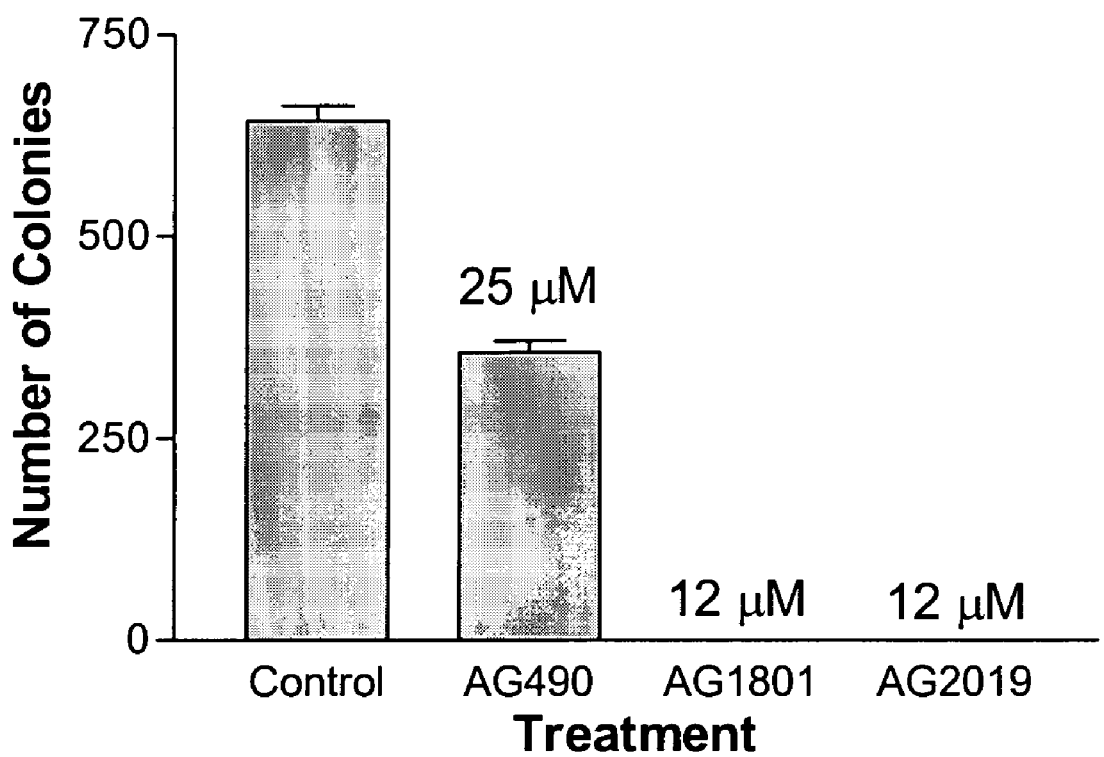
FIG. 1: Inhibition of MM colony formation by compounds AG490, AG1801 and AG 2019. AG1801 (12 µM) and AG 2019 (12 µM) completely inhibited MM colony formation while AG490 (25 µM) was less effective at higher concentrations.

Previous studies have demonstrated that cytokine pathways that activate transcription factors (e.g., NF-kB, Stat 3) are unregulated or activated by genetic lesions or autocrine/paracrine mechanisms in multiple tumor types (Hallek et al., 1998; Hideshima et al, 2002). These pathways contribute to the tumorigenicity and progression of cancer. In the present invention, several compounds were synthesized, and in vitro screening revealed that these compounds can completely block IL-6 mediated Stat3 activation at low concentrations (~1 µM). In addition, these compounds rapidly suppressed expression of the c-myc proto-oncogene, which is frequently overexpressed, rearranged or mutated in many malignancies (Hallek et al., 1998; Selvanayagam et al., 1988; Jernberg-Wiklund et al., 1992; Kuehl et al., 1997). Structure and activity relationships are described in the present invention for tyrphostin and tryphostin-like compounds. As compared to AG490, these compounds are 20 to 50-fold more active in inhibiting Jak2/Stat3 signaling in IL-6 treated cells and posses rapid c-myc downregulatory activity. These compounds can also induce apoptosis of c-myc overexpressing tumor cells at concentrations that parallel their c-myc downregulatory activity. The present invention discloses compounds that inactivate genes and signaling pathways important for tumor cell survival and progression, and these compounds may be used alone or in combination with other agents for the treatment of cancer.

I. Chemical Definitions

Following long-standing patent law convention, the words "a" and "an", when used in the specification including the claims, denotes one or more.

An "alkyl" group refers to a saturated aliphatic hydrocarbon, including straight-chain, branched chain, and cyclic alkyl groups. Preferably, the alkyl group has 1 to 12 carbons. More preferably, it is a lower alkyl of from 1 to 7 carbons, more preferably 1 to 4 carbons. The alkyl group may be substituted or unsubstituted. When substituted, the substituted group(s) is preferably hydroxyl, cyano, alkoxy, =O, =S, $NO_2$, $N(CH_3)_2$, amino, or SH.

An "alkenyl" group refers to an unsaturated hydrocarbon group containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted, the substituted group(s) is preferably hydroxyl, cyano, alkoxy, =O, =S, $NO_2$, $N(CH_3)_2$, halogen, amino, or SH.

An "alkynyl" group refers to an unsaturated hydrocarbon group containing at least one carbon-carbon triple bond, including straight-chain, branched chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted, the substituted group(s) is preferably hydroxyl, cyano, alkoxy, =O, =S, $NO_2$, $N(CH_3)_2$, amino, or SH.

An "alkoxy" group refers to an "—O-alkyl" group, where "alkyl" is defined above.

An "aryl" group refers to an aromatic group which has at least one ring having a conjugated pi electron system, and includes carbocyclic aryl, heterocyclic aryl, and biaryl groups, all of which may be optionally substituted. Preferably, the aryl is a substituted or unsubstituted phenyl or pyridyl. Preferred aryl substituent(s) are halogen, trihalomethyl, hydroxyl, SH, OH, $NO_2$, amine, thioether, cyano, alkoxy, alkyl, and amino groups.

An "alkylaryl" group refers to an alkyl (as described above), covalently joined to an aryl group (as described above). Preferably, the alkyl is a lower alkyl.

"Carbocyclic aryl" groups are groups wherein the ring atoms on the aromatic ring are all carbon atoms. The carbon atoms are optionally substituted with preferred groups as described for aryl groups above.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazoyl, and the like, all optionally substituted.

An "amide" refers to a —C(O)—NH—R, where R is either alkyl, aryl, alkylaryl, or hydrogen.

A "thioamide" refers to a —C(S)—NH—R, where R is either alkyl, aryl, alkylaryl, or hydrogen.

An "ester" refers to a —C(O)—OR', where R' is either alkyl, aryl, or alkylaryl.

An "amine" refers to a —N(R")R'", where R" and R'" is each independently either hydrogen, alkyl, aryl, or alkylaryl, provided that R" and R'" are not both hydrogen.

A "thioether" refers to —S—R, where R is either alkyl, aryl, or alkylaryl.

A "sulfonyl" refers to —S(O)$_2$—R, where R is aryl, C(CN)=C-aryl, $CH_2$—CN, alkylaryl, NH-alkyl, NH-alkylaryl, or NH-aryl.

II. Tyrphostin and Tyrphostin-Like Compounds

The present invention provides tyrphostin and tyrphostin-like compounds for the treatment of cell proliferative diseases such as cancer. Compounds of the present invention include compounds comprising the chemical formula:

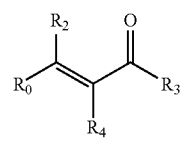

wherein $R_0$ is selected from the group consisting of $R_1$ and $R_1$-$Z_1$-; and wherein $Z_1$ is alkyl; and wherein $R_1$ is chosen from the group consisting of:

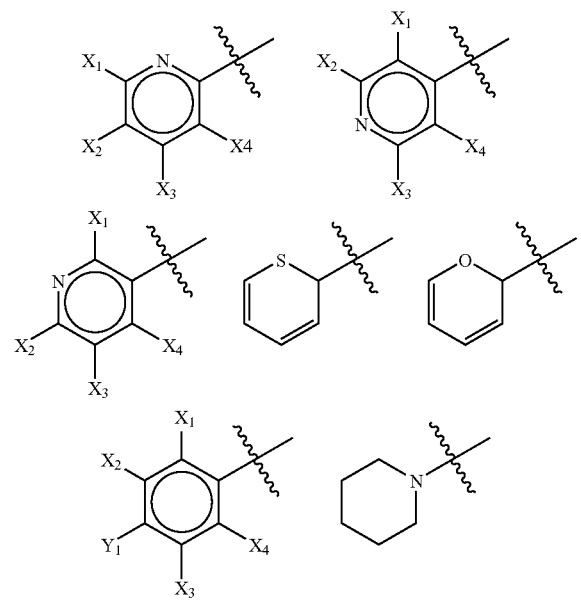

where $X_1$, $X_2$, $X_3$, and $X_4$, are each independently selected from the group consisting of hydrogen, halogen, alkyl, alkoxy, OH, trihalomethyl, and $NO_2$;

where $Y_1$ is selected from the group consisting of halogen and $O_2N$; and $R_2$ is selected from the group consisting of alkyl, alkenyl, alkynyl, alkoxy, alkylaryl, halogen, hydrogen, OH, $NO_2$, thioether, amine, SH, and $NH_2$;

$R_3$ is selected from the group consisting of:

[structures shown: N-containing bicyclic structures (tetrahydroisoquinoline and isoindoline); a structure with $X_5$, $X_6$, Z, and phenyl; a structure with N—CH($R_6$)—(CH$_2$)$_{m_1}$]

[structures shown: NH—$R_5$ and NH—$Z_3$—$R_5$]

wherein $Z_3$ is alkyl; and wherein $m_1$=1, 2, 3, or 4; and where $R_4$ is chosen from the group consisting of: CN, substituted amine, CH$_2$S-alkyl, alkyl, and CH$_2$N$_3$;

where $R_5$ and $R_6$ are each independently chosen from the group consisting of:

[three pyridine structures shown: 2-pyridyl, 3-pyridyl, 4-pyridyl]

monosaccharide (e.g., glucose, fructose, galactose, etc.), polysaccharide, monosaccharide derivative (e.g., an acetylated monosaccharide such as acetylated galactose, 1,2,3,4-diisopropylideno-D-galactose) substituted and unsubstituted aryl, and substituted and unsubstituted alkylaryl;

where Z is selected from the group consisting of NH, S, and O, and where $X_5$ and $X_6$ are each independently chosen from the group consisting of hydrogen and lower alkyl.

In certain embodiments of the present invention, $R_4$ is CN. In certain embodiments, $R_1$ may be chosen from the group consisting of:

[structures shown: O-containing ring, S-containing ring, N-containing piperidine, and two pyridine-type structures with $X_1$, $X_2$, $X_3$, $X_4$]

-continued

[pyridine structure with $X_1$, $X_2$, $X_3$, $X_4$]

In more specific embodiments, $R_1$ is:

[pyridine structure with $X_1$, $X_2$, $X_3$, $X_4$]

In certain embodiments, $X_1$ is a halogen such as Br.

$R_5$ may be chosen from the group consisting of an alkylaryl having the structure:

[structure shown: phenyl with $R_7$, $R_8$, $R_9$, $R_{10}$, $R_{11}$ substituents, connected via (CH$_2$)$_m$ with $X_5$, $X_6$]  and an aryl having the structure:

[phenyl structure with $R_7$, $R_8$, $R_9$, $R_{10}$, $R_{11}$]

wherein m=0, 1, 2, 3, 4, 5, 6, or 7 and where $X_5$ and $X_6$ are each independently chosen from the group consisting of hydrogen and alkyl, and where $R_7$, $R_8$, $R_9$, $R_{10}$, and $R_{11}$, are each independently selected from the group consisting of hydrogen, halogen, alkyl, alkoxy, OH, trihalomethyl, and NO$_2$.

In more specific embodiments $R_5$ is an alkylaryl. $X_1$, $X_2$, $X_3$, and $X_4$ may be hydrogen. $Z_1$ may be a lower alkyl, and the lower alkyl may be —(CH$_2$)$_{m3}$—, wherein M3=0, 1, 2, 3, or 4.

$Z_3$ may be a lower alkyl, and the lower alkyl may be —(CH$_2$)$_{m4}$—, wherein M4=0, 1, 2, 3, or 4. $Y_1$ may be O$_2$N or a halogen, such as Cl or Br.

In certain embodiments, $R_5$ is selected from the group consisting of:

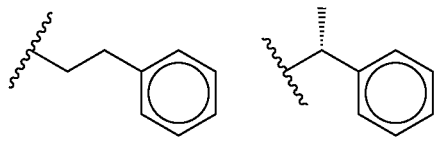

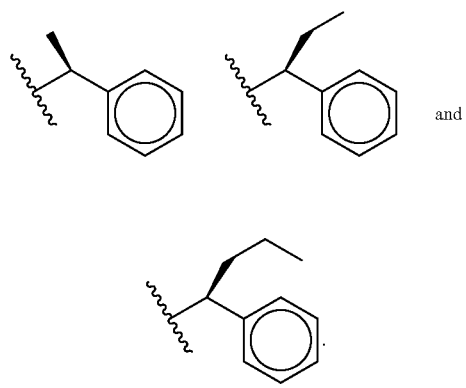

and $R_2$ may be hydrogen. $Y_1$ may be selected from the group consisting of $O_2N$ and a halogen, such as Br or Cl.

Certain embodiments of the present invention relate to a compound having the formula:

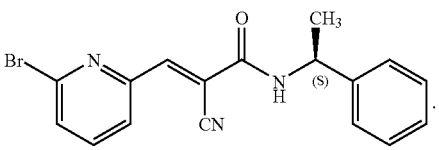

Certain embodiments of the present invention relate to a compound having the formula:

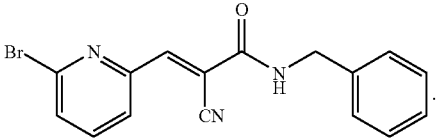

Certain embodiments of the present invention relate to a compound having the formula:

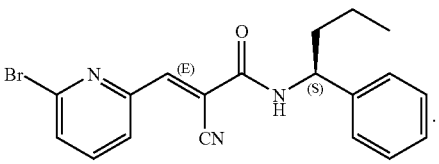

Certain embodiments of the present invention relate to a compound having the formula:

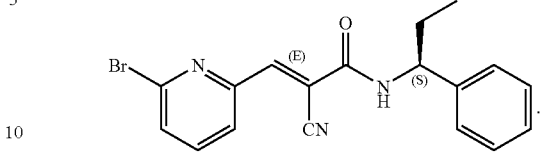

Certain embodiments of the present invention relate to a compound having the formula:

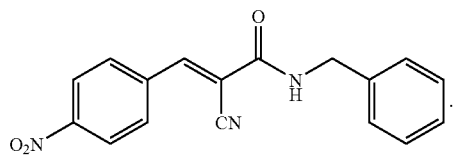

Certain embodiments of the present invention relate to a compound having the formula:

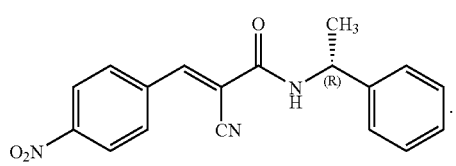

Certain embodiments of the present invention relate to a compound having the formula:

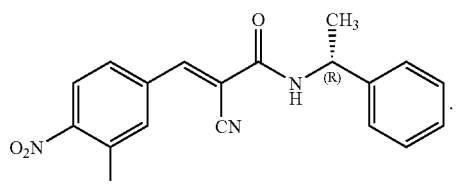

Certain embodiments of the present invention relate to a compound having the formula:

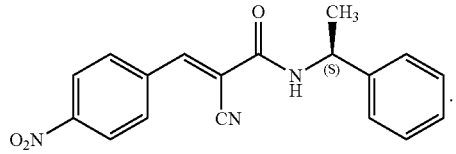

Certain embodiments of the present invention relate to a compound having the formula:

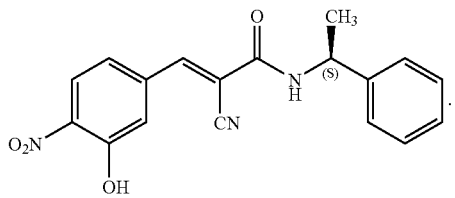

Certain embodiments of the present invention relate to a compound having the formula:

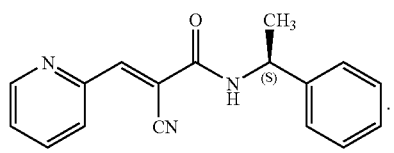

Certain embodiments of the present invention relate to a compound having the formula:

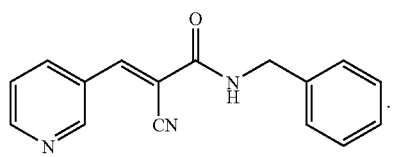

Certain embodiments of the present invention relate to a compound having the formula:

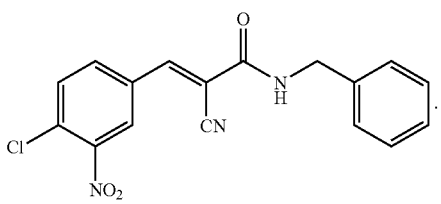

III. Cell Proliferative Diseases

The term "cell proliferative diseases" refers to disorders resulting from abnormally increased and/or uncontrolled growth of cell(s) in a multicellular organism that results in harm (e.g., discomfort or decreased life expectancy) to the multicellular organism. Cell proliferative diseases can occur in animals or humans. Cancer is an example of a cell proliferative disease, and certain embodiments of the present invention are directed towards the treatment of cancer.

In certain embodiments, compounds and methods of the present invention may be used to treat a wide variety of cancerous states including, for example, melanoma, non-small cell lung, small cell lung, lung, hepatocarcinoma, retinoblastoma, astrocytoma, glioblastoma, leukemia, blood, brain, skin, eye, tongue, gum, neuroblastoma, head, neck, breast, pancreatic, renal, bone, testicular, ovarian, mesothelioma, cervical, gastrointestinal, lymphoma, colon, and/or bladder. The cancer may comprise a tumor made of cancer cells. These cancerous states may include cells that are cancerous, pre-cancerous, and/or malignant.

It is also anticipated that compounds of the present invention may also be used to treat cell proliferative diseases other than cancer. Other cell proliferative diseases that may be treated in certain embodiments of the present invention include, for example, rheumatiod arthritis, inflammatory bowel disease, osteoarthritis, leiomyomas, adenomas, lipomas, hemangiomas, fibromas, vascular occlusion, restenosis, artherosclerosis, pre-neoplastic lesions (e.g., adenomatous hyperplasia, prostatic intraepithelial neoplasia), carcinoma in situ, oral hariy leukoplakia and/or psoriasis.

Additionally, compounds of the present invention may be used to treat diseases other than hyperproliferative diseases. For example, certain tyrphostins may be useful for the treatment of hypertrophy and ischemia (U.S. Pat. No. 6,433,018) as well as hepatitis B infection (U.S. Pat. No. 6,420,338). Thus compounds of the present invention may also be useful for the treatment of other diseases including hypertrophy, ischemia, and a viral infection (e.g., hepatitis B infection).

IV. Pharmaceutical Compositions

The anti-tumor compounds of this invention can be administered to kill certain cells involved in a cell proliferative disease, such as tumor cells, by any method that allows contact of the active ingredient with the agent's site of action in the tumor. They can be administered by any conventional methods available for use in conjunction with pharmaceuticals, either as individual therapeutically active ingredients or in a combination of therapeutically active ingredients. They can be administered alone but are generally administered with a pharmaceutically acceptable carrier selected on the basis of the chosen route of administration and standard pharmaceutical practice.

Aqueous compositions of the present invention will have an effective amount of the compounds to kill or slow the growth of cancer cells. Such compositions will generally be dissolved or dispersed in a pharmaceutically acceptable carrier or aqueous medium.

The terms "AG compounds" and "WP compounds" refer to specific examples of the present invention. For example compound WP1015 is an example of a WP compound, and AG1801 is an example of an AG compound.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants, lipid carriers, liposomes and the like.

A. Parenteral Administration

The active compounds will often be formulated for parenteral administration, e.g., formulated for injection via the intravenous, intramuscular, subcutaneous, or even intraperitoneal routes. The preparation of an aqueous composition that contains an anthracycline of the present invention as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some forms, it will be desirable to formulate the compounds in salt form, generally to improve the solubility and bioavailability and to provide an active drug form more readily assimilated. As used herein, the term "pharmaceutically acceptable salt" refers to compounds which are formed from acidifying a substituted anthracycline solution with suitable physiologically tolerated acids. Suitable physiologically tolerated acids are organic and inorganic acids, such as hydrochloric acid, sulfuric acid, phosphoric acid, acetic acid, citric acid, oxalic acid, malonic acid, salicylic acid, maleic acid, methane sulfonic acid, isothionic acid, lactic acid, gluconic acid, glucuronic acid, amidosulfuric acid, benzoic acid, tartaric acid and pamoaic acid. Typically, such salt forms of the active compound will be provided or mixed prior to use.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like.

The compounds of the present invention may also be formulated into a composition comprising liposomes or any other lipid carrier. Liposomes include: multivesicular liposomes, multilamellar liposomes, and unilamellar liposomes.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in creams and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

B. Oral Administration

In certain embodiments, active compounds may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, such as those described below in specific examples.

IV. Therapies

One of the major challenges in oncology today is the effective treatment of a given tumor. Tumors are often resistant to traditional therapies. Thus, a great deal of effort is being directed at finding efficacious treatment of cancer. One way of achieving this is by combining new drugs with the traditional therapies. In the context of the present invention, it is contemplated that therapies using the compounds could be used in combination with surgery, chemotherapy, radiotherapy, and/or a gene therapy.

"Effective amounts" or a "therapeutically relevant amount" are those amounts of a compound sufficient to produce a therapeutic benefit (e.g., effective to reproducibly inhibit decrease, reduce, inhibit or otherwise abrogate the growth of a cancer cell). An effective amount, in the context of treating a subject, is sufficient to produce a therapeutic benefit. The term "therapeutic benefit" as used herein refers to anything that promotes or enhances the well-being of the subject with respect to the medical treatment of the subject's cell proliferative disease. A list of nonexhaustive examples of this includes extension of the patients life by any period of time; decrease or delay in the neoplastic development of the disease; decrease in hyperproliferation; reduction in tumor growth; delay of metastases; reduction in the proliferation rate of a cancer cell, tumor cell, or any other hyperproliferative cell; induction of apoptosis in any treated cell or in any cell affected by a treated cell; and/or a decrease in pain to the subject that can be attributed to the patient's condition.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

General Method for Synthesis of Compounds

N-(Phenylalkyl)cinnamides were prepared by the following general procedure. Benzylamine (3.0 g, 28 mmol) and ethyl cyanoacetate (4.7 g, 42 mmol) in acetonitrile (20 mL) was stirred and reflux for 4 hr. Benzylamine in this general procedure can be replaced by any other substituents depicted as $R_3$ above. The solvent was removed in vacuo to give an oil which solidified upon standing. Precipitation (EtOAc) resulted in 3.28 g (68%) of an off-white powder corresponding to N-benzylcyanoacetamide as an intermediate. A mixture of N-benzylcyanomethylamide (1.3, 7.5 mmol), 3,4-dihydroxybenzaldehyde (1.1 g, 8.2 mmol), and piperidine (catalytic, 5 drops) was stirred at reflux for 3 hr. Flash chromatography (EtOAc) followed by two recrystalizations ($H_2O$/EtOH) yielded product as a white powder 0.8 g (36%).

EXAMPLE 2

Synthesis of Compounds

Using the protocol detailed in Example 1, the following compounds were synthesized, and data regarding the synthesis of these compounds are presented below.

AG1801 was synthesized. $^1$H-NMR (CDCl$_3$, 500 MHz, δ): 8.49 (s, 1H, H-3), 7.39 (d, 2H, J=8.7 Hz, H-3',5'), 8.12 (d, 2H, J=7.5 Hz, H-2',6'), 7.43-7.39 (5H, H aromat. from benzyl), 6.75 (bs, 1H, NH), 4.68 (d, 2H, J=5.7 Hz, CH$_2$). Elemental. Anal. Calcd. For C$_{17}$H$_{13}$N$_3$O$_3$, Theor. C, 66.44; H, 4.26, N, 13.67. Found: C, 65.70; H, 4.27, N, 13.45. m.p. 165-166° C.

WP1002 was synthesized. $^1$H-NMR (CDCl$_3$, 500 MHz, δ): 8.23 (s, 1H, H-3), 7.83 (d, 2H, J=8.6 Hz, H-2',6'), 7.39-7.28 (5H, H aromat. from benzyl), 6.69 (d, 2H, J=8.6 Hz, H-3',5'), 6.58 (bs, 1H, NH), 4.62 (d, 2H, J=5.7 Hz, CH$_2$). 4.30 (bs, 2H, NH$_2$)

WP1003 was synthesized. $^1$H-NMR (CDCl$_3$, 500 MHz, δ): 8.30 (s, 1H, H-3), 7.92 (d, 2H, J=8.7 Hz, H-2',6'), 7.71 (s, 1H, NH), 7.66 (d, 2H, J=8.4 Hz, H-3',5'), 7.42-7.28 (5H, H aromat. from benzyl), 6.70 (bs, 1H, NH), 4.62 (d, 2H, J=5.7 Hz, CH$_2$). 2.22 (s, 3H, CH$_3$)

WP1004 was synthesized. $^1$H-NMR (CDCl$_3$, 500 MHz, δ): 8.30 (s, 1H, H-3), 7.94 (d, 2H, J=8.7 Hz, H-2',6'), 7.68 (d, 2H, J=8.6 Hz, H-3',5'), 7.51 (s, 1H, NH), 7.43-7.39 (5H, H aromat. from benzyl), 6.67 (t, 1H, J=5.3 Hz, NH), 4.62 (d, 2H, J=5.7 Hz, CH$_2$). 2.41 (t, 2H, J=7.4 Hz, CH$_2$), 1.73 (m, 2H, CH$_2$), 1.42 (m, 2H, CH$_2$), 0.96 (t, 3H, J=7.4 Hz, CH$_3$)

WP1005 was synthesized. $^1$H-NMR (CDCl$_3$, 500 MHz, δ): 8.31 (s, 1H, H-3), 7.94 (d, 2H, J=8.7 Hz, H-2',6'), 7.68 (d, 2H, J=8.6 Hz, H-3',5'), 7.41 (s, 1H, NH), 7.40-7.28 (5H, H aromat. from benzyl), 6.66 (t, 1H, J=5.7 Hz, NH), 5.35 (m, 2H, CH=CH), 4.62 (d, 1H, J=5.7 Hz, CH$_2$). 2.40 (t, 2H, J=7.4 Hz, CH$_2$), 1.73 (m, 4H, CH$_2$), 1.75 (m, 2H, CH$_2$), 1.31 (m, 22H, CH$_2$), 0.89 (t, 3H, J=7.0 Hz, CH$_3$)

WP1009 was synthesized. $^1$H-NMR (CDCl$_3$, 400 MHz, δ): 11.88 (bs, 1H, H-1'), 8.64 (t, 1H, J=5.8 Hz, NH), 8.07 (s, 1H, H-3), 7.36-7.22 (m, 7H, H-3', 5' and Haromat. from benzyl), 6.41 (bs, 1H, H-4'), 4.39 (d, 2H, J=6.0 Hz, CH$_2$). m.p. 216-217° C.

WP1010 was synthesized. $^1$H-NMR (DMSO-d$_6$, 500 MHz, δ): 10.42 (bs, 1H, NHSO$_2$Me), 8.94 (bs, 1H, NH), 8.15 (s, 1H, H-3), 7.98 (d, 2H, J=8.5 Hz, H-2',6'), 7.43-7.39 (7H, H-3',5' and H aromat. from benzyl), 4.43 (d, 1H, J=5.4 Hz, CH$_2$), 3.15 (s, 3H. Me).

WP1006 was synthesized. $^1$H-NMR (CDCl$_3$, 500 MHz, δ): 8.35 (s, 1H, H-3), 7.98 (ddd, 2H, J=8.6 Hz, J=5.4 Hz, J=5.1

Hz, H-2',6'), 7.40-7.31 (5H, H aromat. from benzyl), 7.20 (dd, 2H, J=8.5 Hz, J=11.5 Hz, H-3',5'), 6.71 (bs, 1H, NH), 4.62 (d, 2H, J=5.8 Hz, CH$_2$). Elemental. Anal. Calcd. for C$_{17}$H$_{13}$FN$_2$O, Theor. C, 72.85; H, 4.67; F, 6.78, N, 9.99. Found: C, 72.86; H, 4.65; F, 6.68; N, 9.80. m.p. 150-151° C.

WP1007 was synthesized. $^1$H-NMR (CDCl$_3$, 500 MHz, δ): 8.33 (s, 1H, H-3), 8.00 (d, 2H, J=8.6 Hz, H-3',5'), 7.40-7.27 (5H, H aromat. from benzyl), 7.14 (dd, 2H, J=7.0 Hz, J=1.9 Hz, H-2',6'), 6.66 (bs, 1H, NH), 4.63 (d, 1H, J=5.8 Hz, CH$_2$). m.p. 147-149° C.

WP1011 was synthesized. $^1$H-NMR (CDCl$_3$, 300 MHz, δ): 8.31 (s, 1H, H-3), 7.98 (d, 2H, J=8.6 Hz, H-3',5'), 7.63 (d, 2H, J=8.5 Hz, H-2',6'), 7.40-7.26 (5H, H aromat. from benzyl), 6.67 (bs, 1H, NH), 4.61 (d, 2H, J=5.8 Hz, CH$_2$). m.p. 177-178° C.

WP1012 was synthesized. $^1$H-NMR (DMSO-d$_6$, 300 MHz, δ): 11.58 (bs, 1H, H-1'), 8.86 (t, 1H, J=5.7 Hz, NH), 8.28 (s, 1H, H-3), 8.25 (bs, 1H, H-4'), 7.83 (dd, 1H, J=8.6 Hz, J=1.7 Hz, H-8'), 7.57 (d, 1H, J=8.7 Hz, H-7'), 7.50 (dd, 1H, J=2.8 Hz, H-2'), 7.35-7.21 (m, 5H, H aromat. from benzyl), 6.60 (bs, 1H, H-3'), 4.44 (d, 2H, J=5.7 Hz, CH$_2$). m.p. 199-200° C.

WP1013 was synthesized. $^1$H-NMR (CDCl$_3$, 400 MHz, δ): 10.93 (s, 1H, OH), 8.66 (d, 1H, J=2.3 Hz, H-6), 8.31 (s, 1H, H-7), 8.26 (dd, 1H, J=8.9 Hz, J=2.2 Hz, H-2), 7.40-7.29 (6H, H-3 and H aromat. from benzyl), 6.66 (bs, 1H, NH), 4.61 (d, 1H, J=5.7 Hz, CH$_2$). m.p. 158-159° C.

WP1014 was synthesized. $^1$H-NMR (CDCl$_3$, 400 MHz, δ): 10.56 (s, 1H, OH), 8.33 (s, 1H, H-3), 8.23 (d, 1H, J=8.8 Hz, H-3'), 7.63 (d, 2H, J=2.0 Hz, H-6'), 7.51 (dd, 1H, J=8.8 Hz, J=2.0 Hz, H-2'), 7.40-7.31 (5H, H aromat. from benzyl), 6.71 (bs, 1H, NH), 4.62 (d, 2H, J=6.0 Hz, CH$_2$). Elemental. Anal. Calcd. For C$_{17}$H$_{13}$N$_3$O$_4$, Theor. C, 63.16; H, 4.05, N, 13.00. Found: C, 62.88; H, 4.15, N, 12.80. m.p. 171-172° C.

WP1015 was synthesized. $^1$H-NMR (CDCl$_3$, 400 MHz, δ): 8.26 (s, 1H, H-3), 7.67 (dd, 1H, J=7.6 Hz, H-5'), 7.60 (dd, 1H, J=7.4 Hz, J=1 Hz, H-4'), 7.58 (dd, 1H, J=7.7 Hz, J=1 Hz, H-6'), 7.40-7.26 (m, 5H, H, H aromat. from benzyl), 6.91 (bs, 1H, NH), 4.62 (d, 2H, J=5.8 Hz, CH$_2$). m.p. 182-183° C.

WP1016 was synthesized. $^1$H-NMR (CDCl$_3$, 400 MHz, δ): 8.50 (s, 1H, H-3), 8.43 (dd, 1H, J=6.8 Hz, J=2.2 Hz, H-6'), 7.81 (ddd, 1H, J=8.7 Hz, J=5.2 Hz, J=2.0 Hz, H-3'), 7.40-7.31 (m, 5H, H arom. from benzyl), 6.96 (dd, 1H, J=9.7 Hz, J=8.7 Hz, H-4'), 6.68 (bs, 1H, NH), 4.62 (d, 2H, J=5.7 Hz, CH$_2$). Elemental. Anal. Calcd. For C$_{17}$H$_{12}$FIN$_2$O, Theor. C, 50.27; H, 2.98; F, 4.68; I, 31.24; N, 6.90. Found: C, 50.68; H, 3.22; N, 6.73; F, 4.46; I, 30.33. m.p. 138-139° C.

WP1017 was synthesized. $^1$H-NMR (CDCl$_3$, 400 MHz, δ): 8.50 (s, 1H, H-3), 8.43 (dd, 1H, J=6.8 Hz, J=2.2 Hz, H-6'), 7.81 (ddd, 1H, J=8.7 Hz, J=5.2 Hz, J=2.0 Hz, H-3'), 7.40-7.31 (m, 5H, H arom. from benzyl), 6.96 (dd, 1H, J=9.7 Hz, J=8.7 Hz, H-4'), 6.68 (bs, 1H, NH), 4.62 (d, 2H, J=5.7 Hz, CH$_2$). m.p. 183-184° C.

WP1018 was synthesized. $^1$H-NMR (CDCl$_3$, 400 MHz, δ): 8.38 (s, 1H, H-3), 8.06 (d, 2H, J=8.6 Hz, H-2',6'), 7.93 (s, 1H, H-2''), 7.53 (d, 2H, J=8.6 Hz, H-3',5'), 7.40-7.30 (6H, H-5'' and H aromat. from benzyl), 7.25 (d, 1H, J=4.1 Hz, H-4''), 6.77 (d, 1H, J=6.2 Hz, NH), 4.62 (d, 2H, J=5.8 Hz, CH$_2$). m.p. 187-188° C.

WP1019 was synthesized. $^1$H-NMR (DMSO-d$_6$ 400 MHz, δ): 9.04 (t, 1H, J=6.0 Hz, NH), 8.29 (bs, 2H, OH), 8.22 (s, 1H, H-3), 7.94 (d, 2H, J=8.5 Hz, H-2', 6'), 7.90 (d, 2H, J=8.4 Hz, H-3', 4'), 7.37-7.24 (m, 5H, H aromat. from benzyl), 4.43 (d, 2H, J=5.8 Hz, CH$_2$)

WP1020 was synthesized. $^1$H-NMR (DMSO-d$_6$ 300 MHz, δ): 12.87 (bs, 1H, NH), 12.45 (bs, 1H, NH), 7.82 (s, 1H, H-3), 7.49 (s, 1H, H-3'), 7.26-7.11 (m, 6H, H-5' and H arom from benzyl), 4.37 (d, 2H, J=5.5 Hz, CH$_2$). m.p. 230-231° C.

WP1021 was synthesized. $^1$H-NMR (DMSO-d$_6$, 400 MHz, δ): 12.42 (bs, 1H, H-1'), 8.83 (dd, 1H, J=5.7 Hz, NH), 8.49, 8.47 (2s, 1H ea, H-2',3), 8.01 (d, 1H, J=2.0 Hz, H-4'), 7.56 (d, 1H, J=8.5 Hz, H-7'), 7.33-7.32 (5H, H aromat. from benzyl), 7.26 (dd, 1H, J=8.6 Hz, J=2.1 Hz, H-6'), 4.44 (d, 2H, J=6.0 Hz, CH$_2$). Elemental. Anal. Calcd. For C$_{19}$H$_{14}$ClN$_3$O, Theor. C, 67.96; H, 4.20; Cl, 10.56; N, 12.51. Found: C, 68.15; H, 4.34; Cl, 10.78; N, 12.31. m.p. 229-230° C.

WP1022 was synthesized. $^1$H-NMR (DMSO-d$_6$, 300 MHz, δ): 12.46 (bs, 1H, H'), 8.87 (dd, 1H, J=5.9 Hz, NH), 8.50 (s, 1H, H-3), 8.49 (d, 1H, J=2.6 Hz, H-2'), 8.17 (d, 1H, J=1.7 Hz, H-4'), 7.53 (d, 1H, J=8.6 Hz, H-7'), 7.40 (dd, 1H, J=8.5 Hz, J=2 Hz, H-6'), 7.36-7.23 (5H, H aromat. from benzyl), 4.43 (d, 2H, J=5.9 Hz, CH$_2$). m.p. 224-225° C.

WP1026 was synthesized. $^1$H-NMR (CDCl$_3$, 300 MHz, δ): 8.30 (s, 1H, H-3), 8.01 (s, 1H, H-6'), 7.89 (d, 1H, J=8.0 Hz, H-4'), 7.66 (d, 1H, J=8.1 Hz, H-2'), 7.40-7.30 (m, 6H, H-3' and H aromat. from benzyl), 6.68 (bs, 1H, NH), 4.61 (d, 2H, J=5.7 Hz, CH$_2$). m.p. 150-151° C.

WP1027 was synthesized. $^1$H-NMR (DMSO-d$_6$ 300 MHz, δ): 8.81 (bs, 1H, OH), 8.74 (t, 1H, J=5.8 Hz, NH), 7.32-7.09 (m, 5H, H aromat. from benzyl), 6.66 (d, 1H, J=2.3 Hz, H-2'), 6.64 (d, 1H, J=8.3 Hz, H-5'), 6.50 (dd, 1H, J=8.1 Hz, J=2.1 Hz, H-6'), 4.32 (dd, 1H, J=15.2 Hz, J=6.3 Hz, CH$_2$), 4.22 (dd, 1H, J=15.2 Hz, J=5.5 Hz, CH$_2$), 3.87 (dd, 1H, J=7.1 Hz, CH), 2.98 (dd, 1H, J=13.4 Hz, J=7.3 Hz, 3-CH$_2$), 2.90 (dd, 1H, J=13.4 Hz, J=8.2 Hz, 3-CH$_2$). m.p. 131-132° C.

WP1034 was synthesized. $^1$H-NMR (DMSO-d$_6$, 400 MHz, δ): 8.41 (s, 1H, H-3), 8.33 (d, 2H, J=8.8 Hz, H-3', 5'), 8.05 (d, 2H, J=8.7 Hz, H-2',6'), 7.41-7.26 (m, 5H, H-aromat. from benzyl), 6.60 (d, 1H, J=7.6 Hz, NH), 5.28-5.21 (m, 1H, CH), 1.62 (d, 3H, J=6.9 Hz, CH$_3$). m.p. 172-173° C.

WP1035 was synthesized. $^1$H-NMR (DMSO-d$_6$, 300 MHz, δ): 11.07 (s, 1H, OH), 8.90 (t, 1H, J=5.8 Hz, NH), 8.10 (s, 1H, H-3), 7.85 (dd, 1H, J=12.5 Hz, J=2.1 Hz, H-6'), 7.69 (dd, 1H, J=8.5 Hz, J=2.0 Hz, H-5'), 7.37-7.22 (m, 5H, H-arom. from benzyl), 7.12 (d, 1H, J=8.8 Hz, H-2'), 4.41 (d, 2H, J=5.9 Hz, CH$_2$). m.p. 211-212° C.

WP1036 was synthesized. $^1$H-NMR (DMSO-d$_6$, 400 MHz, δ): 10.71 (bs, 1H, OH), 8.86 (t, 1H, J=6.2 Hz, NH), 8.05 (s, 1H, H-3), 7.96 (d, 1H, J=1.9 Hz, H-2'), 7.66 (d, 1H, J=2.0 Hz, H-6'), 7.34-7.21 (m, 5H, H arom. from benzyl), 4.40 (d, 2H, J=5.8 Hz, CH$_2$), 3.85 (s, 3H, OMe). m.p. 206-207° C.

WP1037 was synthesized. $^1$H-NMR (CDCl$_3$, 500 MHz, δ): 7.37-7.21 (m, 5H, H aromat. from benzyl), 7.11 (d, 1H, J=11.4 Hz, H-3) 6.40 (bs, 1H, NH), 4.56 (d, 1H, J=5.8 Hz, CH$_2$), 2.10-2.03 (m, 1H, H-1'), 1.30 (ddd, 2H, J=12.8 Hz, J=7.6 Hz, J=5.0 Hz, CH$_2$), 0.98 (ddd, 2H, J=8.9 Hz, J=7.3 Hz, J=4.6 Hz, CH$_2$). m.p. 106-107° C.

WP1038 was synthesized. $^1$H-NMR (CDCl$_3$, 400 MHz, δ): 10.54 (s, 1H, OH), 8.27 (s, 1H, H-3), 8.21 (d, 1H, J=8.8 Hz, H-5'), 7.60 (d, 1H, J=2.2 Hz, H-2'), 7.50 (dd, 1H, J=8.9 Hz, J=2.0 Hz, H-6'), 7.40-7.20 (5H, H aromat. from benzyl), 6.60 (d, 1H, J=6.5 Hz, NH), 5.28-5.21 (m, 1H, CH), 1.60 (d, 1H, J=6.9 Hz, CH$_3$). m.p. 178-179° C.

WP1040 was synthesized. $^1$H-NMR (DMSO-d$_6$, 400 MHz, δ): 10.07, 9.54 (2s, 1H ea, OH), 8.62 (d, 1H, J=7.8 Hz, NH), 7.92 (s, 1H, H-3), 7.52 (d, 1H, J=2.0 Hz, H-2'), 7.37-7.20 (5H, H aromat. from benzyl), 7.26 (dd, 1H, J=8.3 Hz, J=2.1 Hz, H-6'), 6.86 (d, 1H, J=8.3 Hz, H-5'), 5.06-4.99 (m, 1H, CH), 1.45 (d, 1H, J=7 Hz, CH$_3$). m.p. 141-142° C.

WP1041 was synthesized. $^1$H-NMR (CDCl$_3$, 500 MHz, δ): 8.20 (s, 1H, H-3), 7.98 (d, 2H, J=9 Hz, H-2',6'), 7.37-7.28 (m, 5H, H-arom. from benzyl), 6.69 (d, 2H, J=9 Hz, H-3',5'), 6.54 (bs, 1H, NH), 4.59 (d, 2H, J=5.7 Hz, CH$_2$), 3.09 (s, 6H, CH$_3$N). m.p. 185-186° C.

WP1042 was synthesized. $^1$H-NMR (CDCl$_3$, 400 MHz, δ): 8.27 (s, 1H, H-3), 7.69 (d, 1H, J=2.1 Hz, H-6'), 7.44-7.26 (12H, H-2', 5' and H aromat. from benzyls), 6.95 (d, 1H, J=8.4 Hz, H-3'), 6.6 (t, 1H, J=5.7 Hz, NH), 5.24 (s, 2H, H-7'), 4.61 (d, 2H, J=5.7 Hz, CH$_2$), 3.94 (s, 3H, OMe). m.p. 132-133° C.

WP1043 was synthesized. $^1$H-NMR (CDCl$_3$, 400 MHz, δ): 8.72 (d, 1H. J=1.7 Hz, H-4'), 8.55 (s, 1H, H-3), 8.15 (m, 2H, H-5, H-2'), 7.54 (ddd, 1H, J=8.2 Hz, J=1.3 Hz, H-6'), 7.46 (m, 2H, H-1', 8'), 7.38-7.29 (m, 6H, H-7' and H aromat. from benzyl), 6.66 (t, 1H, J=5.0 Hz, NH), 4.65 (d, 2H, J=5.7 Hz, CH$_2$), 4.40 (q, 2H, J=7.3 Hz, H-10'), 1.47 (t, 3H, H-11'). m.p. 182-183° C.

WP1044 was synthesized. $^1$H-NMR (CDCl$_3$, 400 MHz, δ): 8.25 (s, 1H, H-3), 8.00 (s, 1H, H-2'), 7.54 (d, 1H, J=2 Hz, H-5'), 7.39-7.29 (5H, H aromat. from benzyl), 7.18 (d, 1H, J=2 Hz, H-4'), 6.56 (bs, 1H, NH), 4.59 (d, 2H, J=5.7 Hz, CH$_2$). m.p. 188-189° C.

WP1049 was synthesized. $^1$H-NMR (DMSO-d$_6$, 500 MHz, δ): 8.75 (t, 1H, J=5.8 Hz, NH), 8.26 (dd, 2H, J=8.8 Hz, J=1.9 Hz, H-3',5'), 7.84 (dd, 2H, J=8.7 Hz, J=2.4 Hz, H-2',6'), 7.59 (d, 1H, J=15.9 Hz, H-3), 7.38-7.24 (m, 5H, H arom from benzyl), 6.89 (d, 1H, J=15.9 Hz, H-2), 4.43 (d, 2H, J=5.9 Hz, CH$_2$). m.p. 193-194° C.

WP1050 was synthesized. $^1$H-NMR (CDCl$_3$, 400 MHz, δ): 8.38 (s, 1H, H-3), 8.33 (d, 2H, J=8.9 Hz, H-3',5'), 8.04 (d, 2H, J=8.9 Hz, H-2',6'), 7.41-7.29 (5H, H aromat. from benzyl), 6.60 (d, 1H, J=8.2 Hz, NH), 5.28-5.21 (m, 1H, CH), 1.62 (d, 3H, J=7.0 Hz, CH$_3$). m.p. 173-174° C.

WP1051 was synthesized. $^1$H-NMR (CDCl$_3$, 400 MHz, δ): 10.56 (bs, 1H, OH), 8.28 (s, 1H, H-3), 8.21 (d, 1H, J=8.8 Hz, H-5'), 7.61 (d, 1H, J=1.8 Hz, H-2'), 7.50 (dd, 1H, J=8.8 Hz, J=1.8 Hz, H-6'), 7.41-7.30 (5H, H aromat. from benzyl), 6.62 (d, 1H, J=8.0 Hz, NH), 5.27-5.21 (m, 1H, CH), 1.61 (d, 3H, J=6.9 Hz, CH$_3$). m.p. 176-177° C.

WP1052 was synthesized. $^1$H-NMR (CDCl$_3$, 400 MHz, δ): 10.93 (s, 1H, OH), 8.64 (d, 1H, J=2.3 Hz, H-2'), 8.25 (s, 1H, H-3), 8.24 (dd, 1H, J=8.9 Hz, J=2.3 Hz, H-6'), 7.40-7.28 (6H, H-5' and H aromat. from benzyl), 6.54 (d, 1H, J=6.4 Hz, NH), 5.28-5.21 (m, 1H, CH), 1.61 (d, 3H, J=6.9 Hz, CH$_3$). m.p. 182-183° C.

WP1053 was synthesized. $^1$H-NMR (CDCl$_3$, 400 MHz, δ): 8.34 (s, 1H, H-3), 8.57 (dd, 1H, J=2.1 Hz, H-6'), 7.50 (d, 1H, J=7.8 Hz, H-2'), 7.40-7.30 (10H, H aromat. from benzyls), 7.16 (dd, 1H, J=7.5 Hz, J=2.4 Hz, H-3'), 6.67 (bs, 1H, NH), 5.12 (s, 2H, H-7'), 4.62 (d, 2H, J=5.7 Hz, CH$_2$). m.p. 190-191° C.

WP1054 was synthesized. $^1$H-NMR (DMSO-d$_6$, 500 MHz, δ): 11.4 (s, 1H, OH), 8.89 (t, 1H, J=5.8 Hz, NH), 8.09 (s, 1H, H-3), 8.05 (d, 1H, J=2.2 Hz, H-2'), 7.83 (dd, 1H, J=8.7 Hz, J=2.2 Hz, H-6'), 7.40-7.22 (5H, H aromat. from benzyl), 7.12 (d, 1H, J=8.6 Hz, H-5'), 4.41 (d, 1H, J=5.9 Hz, CH$_2$). m.p. 213-214° C.

WP1055 was synthesized. $^1$H-NMR (DMSO-d$_6$, 300 MHz, δ): 9.06 (t, 1H, J=5.8 Hz, NH), 8.77 (d, 1H, J=4.6 Hz, H-3'), 8.18 (s, 1H, H-3), 7.99 (ddd, 1H, J=7.8 Hz, J=2.2 Hz, H-5'), 7.85 (d, 1H, J=7.7 Hz, H-6'), 7.55 (dd, J=7.5 Hz, J=4.9 Hz. H-4'), 7.38-7.23 (5H, H aromat. from benzyl), 4.44 (d, 1H, J=5.9 Hz, CH$_2$). m.p. 184-185° C.

WP1060 was synthesized. $^1$H-NMR (CDCl$_3$, 300 MHz, δ): 8.13 (d, 2H, J=8.7 Hz, J=2.4 Hz, H-3', 5'), 7.42 (d, 2H, J=8.7 Hz, H-2', 6'), 7.37-7.17 (m, 5H, H arom from benzyl), 6.78 (bs, 1H, NH), 4.69 (dd, 1H, J=7.1 Hz, J=4.5 Hz, H-2), 4.49 (dd, 1H, J=14.7 Hz, J=6.1 Hz, CH$_2$), 4.39 (dd, 1H, J=14.7 Hz, J=5.7 Hz, CH$_2$), 3.55 (dd, 1H, J=14.2 Hz, J=4.5 Hz H-3), 3.46 (dd, 1H, J=14.2 Hz, J=7.1 Hz H-3). m.p. 129-130° C.

WP1063 and WP1064 were synthesized. $^1$H-NMR (DMSO-d$_6$, 300 MHz, δ): 8.23 (t, 1H, J=6.1 Hz, NH), 8.16 (d, 2H, J=8.8 Hz, H-3', 5'), 7.64 (d, 2H, J=8.6 Hz, H-2', 6'), 7.29-7.18 (m, 5H, Harom from benzyl), 5.68 (d, 1H, J=6.2 Hz, OH), 5.49 (d, 1H, J=6.9 Hz, OH), 5.07 (dd, 1H, J=6.1 Hz, J=2.9 Hz, CH), 4.31 (d, 2H, J=3.9 Hz, CH$_2$), 4.09 (dd, 1H, J=7.0 Hz, J=2.9 Hz, CH). m.p. 160-161° C.

WP1065 was synthesized. $^1$H-NMR (CDCl$_3$, 300 MHz, δ): 8.81 (d, 1H, J=4.3 Hz, H-3'), 8.30 (s, 1H, H-3), 7.80 (ddd, 1H, J=7.7 Hz, J=0.8 Hz, H-5'), 7.61 (d, 1H, J=7.7 Hz, H-6'), 7.42-7.28 (m, 6H, H-4' and H aromat. from benzyl), 6.79 (d, 1H, J=6.8 Hz, NH), 5.30-5.21 (m, 1H, CH), 1.61 (d, 3H, J=6.9 Hz, CH$_3$). m.p. 153-154° C.

WP1066 was synthesized. $^1$H-NMR (CDCl$_3$, 300 MHz, δ): 8.20 (s, 1H, H-3), 7.66 (dd, 1H, J=7.6 Hz, H-5'), 7.59-7.56 (m, 2H, H-4', 6'), 7.37-7.26 (m, 5H, H aromat. From benzyl), 6.80 (d, 1H, J=7.0 Hz, NH), 5.29-5.20 (m, 1H, CH), 1.61 (d, 3H, J=6.9 Hz, CH$_3$). m.p. 143-144° C.

WP1067 was synthesized. $^1$H-NMR (CDCl$_3$, 400 MHz, δ): 8.80 (s, 1H, H-3), 8.27 (dd, 1H, J=7.8 Hz, J=0.6 Hz, H-3'), 7.80-7.76 (m, 2H, H-5', 6'), 7.72-7.67 (m, 1H, H-4'), 7.41-7.26 (m, 5H, H aromat. from benzyl), 6.69 (bs, 1H, NH), 4.62 (d, 1H, J=5.7 Hz, CH$_2$).

WP1069 was synthesized. $^1$H-NMR (CDCl$_3$, 300 MHz, δ): 9.09 (d, 1H, J=2.2 Hz, H-3'), 8.80 (s, 1H, H-3), 8.62 (dd, 1H, J=8.5 Hz, J=2.3 Hz, H-5'), 7.97 (d, 1H, J=8.5 Hz, H-6'), 7.42-7.31 (m, 6H, H aromat. from benzyl), 6.69 (bs, 1H, NH), 4.63 (d, 2H, CH$_2$).

WP1076 was synthesized. $^1$H-NMR (CDCl$_3$, 400 MHz, δ): 8.59 (s, 1H, H-3), 8.01 (d, 1H, J=9.0 Hz, H-6'), 7.39-7.31 (m, 5H, H aromat. from benzyl), 4.77 (d, 1H, J=2.7 Hz, H-3'), 6.89 (dd, 1H, J=8.9 Hz, J=2.7 Hz, H-5'), 6.58 (bs, 1H, NH), 4.60 (d, 2H, J=5.7 Hz, CH$_2$), 3.13 (s, 6H, 2 CH$_3$).

WP1074 was synthesized. $^1$H-NMR (CDCl$_3$, 400 MHz, δ): 8.71 (dd, 1H, J=1.9 Hz, H-2'), 8.44 (s, 1H, H-3), 8.38 (ddd, 1H, J=8.2 Hz, J=2.1 Hz, J=0.8 Hz, H-4'), 8.27 (d, 1H, J=7.8 Hz, H-6'), 7.72 (dd, J=8.0 Hz, H-5'), 7.40-7.30 (m, 5H, H aromat. from benzyl), 6.71 (bs, 1H, NH), 4.63 (d, 1H, J=5.8 Hz, CH$_2$).

WP1073 was synthesized. $^1$H-NMR (DMSO-d$_6$, 400 MHz, δ): 11.44 (bs, 1H, OH), 9.07 (dd, 1H, J=5.9 Hz, NH), 8.59 (s, 1H, H-3), 8.22 (d, 1H, J=9.0 Hz, H-3'), 7.38-7.25 (m, 5H, H aromat. from benzyl), 7.12 (d, 1H, J=2.6 Hz, H-6'), 7.08 (dd, 1H, J=9.1 Hz, J=2.6 Hz, H-4'), 4.44 (d, 2H, J=5.9 Hz, CH$_2$).

WP1077 was synthesized. $^1$H-NMR (CDCl$_3$, 400 MHz, δ): 8.35 (d, 1H, J=2 Hz, H-2'), 8.34 (s, 1H, H-3), 8.09 (dd, 1H, J=8.4 Hz, J=2.4 Hz, H-6'), 7.70 (d, 1H, J=8.4 Hz, H-5'), 7.40-7.26 (m, 5H, H aromat. from benzyl), 6.68 (bs, 1H, NH), 4.62 (d, 2H, J=5.6 Hz, CH$_2$).

WP1075 was synthesized. $^1$H-NMR (DMSO-d$_6$, 400 MHz, δ): 9.08 (dd, 1H, J=6.1 Hz, NH), 8.98 (d, 1H, J=2.3 Hz, H-2'), 4.96 (dd, 1H, J=4.8 Hz, J=1.6 Hz, H-4'), 8.37 (ddd, 1H, J=8.2 Hz, J=2.0 Hz, H-6'), 8.26 (s, 1H, H-3), 7.60 (dd, 1H, J=8.2 Hz, J=4.8 Hz, H-5'), 7.35-7.23 (m, 5H, H aromat. from benzyl), 4.43 (d, 2H, J=6.0 Hz, CH$_2$).

WP1119 was synthesized. $^1$H-NMR (CDCl$_3$, 300 MHz, δ): 8.20 (s, 1H, H-3), 7.70-7.62 (m, 2H, H-4', H-6'), 7.59-7.56 (m, 1H, H-5'), 7.14 (m, 1H, NH), 5.54 (d, 1H, H-1", J=4.97 Hz), 4.63 (dd, 1H, H-3", J=2.23, J=7.94 Hz), 4.32 (dd, 1H, H-2", J=2.23, J=4.97 Hz), 4.29-4.26 (m 1H, H-4"), 4.03-4.00 (m, 1H, H-5"), 3.93-3.85 (m, 1H, H-6"), 3.54-3.45 (m, 1H, H-6"), 1.51 (s, 3H CH$_3$"), 1.49 (s, 3H, CH$_3$"), 1.36 (s, 3H CH$_3$"), 1.32 (s, 3H, CH$_3$").

WP1126 was synthesized. $^1$H-NMR (DMSO, 300 MHz, δ): 8.42 (m, 1H, NH), 8.10 (s, 1H, H-3), 7.97-7.88 (m, 2H, H-4', H-6'), 7.82-7.79 (m, 1H, H-5'), 5.75-6.50 (bs, 1H, OH), 4.94 (d, 1H, H-1", J=2.66 Hz), 4.49-3.77 (m, 3H, OH), 4.02-3.98 (m, 1H), 3.67 (m, 1H), 3.60-3.50 (m 2H), 3.40-3.36 (m, 2H, H-6").

WP1127 was synthesized. $^1$H-NMR (CDCl$_3$, 300 MHz, δ): 8.21 (s, 1H, H-3), 7.72-7.59 (m, 3H, H-4', H-5', H-6'), 6.95-6.91 (m, 1H, NH), 6.41 (m, 1H, H-1"), 5.48 (m, 1H), 5.37 (m, 2H), 4.34-4.29 (m, 1H, H-5"), 3.66-3.47 (m, 2H, H-6"), 2.24 (s, 3H, CH$_3$), 2.17 (s, 3H, CH$_3$), 2.04 (s, 3H, CH$_3$), 2.03 (s, 3H, CH$_3$).

EXAMPLE 3

Compounds Display Potent Anti-Cancer Effects

IL-6 stimulates Stat3 phosphorylation in multiple myeloma (MM) and non-Hodgkin's lymphoma (NHL) cells. In FIG. 1, MM cells (MM-1, 8226, 8226/S, U266) or NHL (DBr, DB, DS, LP, LR, Mino, MS, FN, Jeko, JM) cells were treated with IL-6 (10 ng/ml) for 10 min before cell lysates were prepared and evaluated for Stat3 tyrosine phosphorylation by immunoblot (anti-pY705-Stat3 from Cell Signaling). IL-6 stimulated Stat3 phosphorylation in all MM cell lines and in 5 out of 10 NHL cell lines (specifically, in DB, DS, LP, FN, and JM cells). It should be noted that U266 cells expressed constitutively activated Stat3 that was further stimulated by exogenous addition of IL-6.

To examine the effect of newly synthesized AG and WP compounds on cytokine-mediated Stat activation, multiple myeloma (MM-1) cells were pretreated with AG490 or AG1801 at 2.5, 12, and 25 μM concentrations (for 2 hr) before stimulating cells with IL-6 or IFN-α for 10 min. Stat3 and Stat1 expression and activation were examined by immunoblotting. AG1801 (at 12 and 25 μM) was effective in suppressing IL-6 signaling without effecting IFN-α signaling. AG2019 had similar activity at 12 and 25 μM. AG490 was inactive under these conditions.

To determine whether AG1801 effects caspase activation in MM cells, OCI-My5 cells were treated as described above before cell lysates were examined for casapase activation and PARP cleavage. At 12.5 and 25 μM, AG1801 activated both upstream and downstream caspases (i.e., caspase 3 and caspase 8), and AG1801 increased PARP clevage. At 12.5 and 25 μM, AG490 was ineffective in caspase activation and PARP clevage in these cells.

To determine whether these compounds effect primary MM colony growth bone marrow aspirates from MM patients were partially-purified by magnetic bead separation and analyzed for immunoglobulin heavy-chain gene rearrangement by PCR. Cells were grown as colonies in methyl-cellulose in the presence or absence of AG compound as noted for 7 to 10 day s. Control colonies were examined for Ig heavy chain gene rearrangement to confirm the clonal nature of the population. As shown in FIG. 1, AG1801 and AG 2019 completely inhibited MM colony formation while AG490 was less effective at higher concentrations.

To determine the effect of compounds on both Stat3 activation and c-myc protein expression MM-1, OCI-My5 and U266 cells were incubated with 25 μM of AG1801, AG490, WP1038, WP1039, WP1051, or WP1052 for 2 hours before cells were stimulated with 2 ng/ml IL-6 for 10 min. Cell lysates were prepared and immunoblotted for p-Stat3, Stat3, c-myc and actin (as a control). Both Stat3 activation and c-myc expression were effected by WP and AG compounds. IL-6 stimulated Stat3 activation but did not significantly c-myc expression.

Figure 2A:
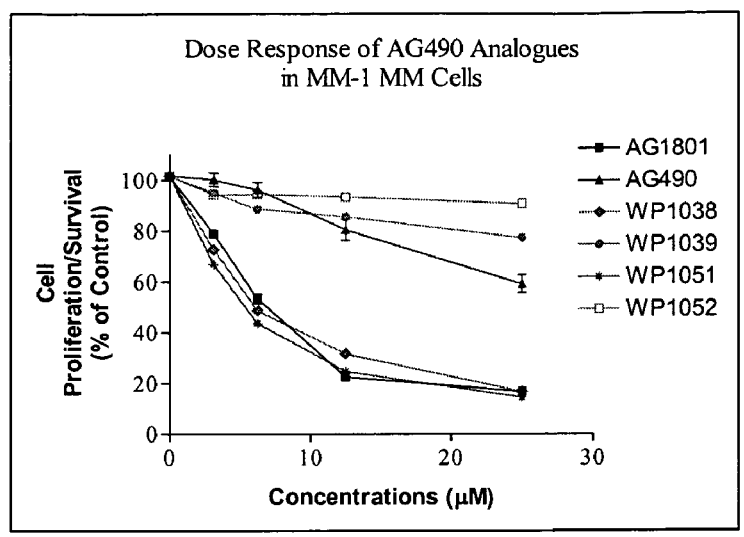
FIGS. 2A-C: Inhibition of growth and survival of MM cell lines.
Figure 2B:
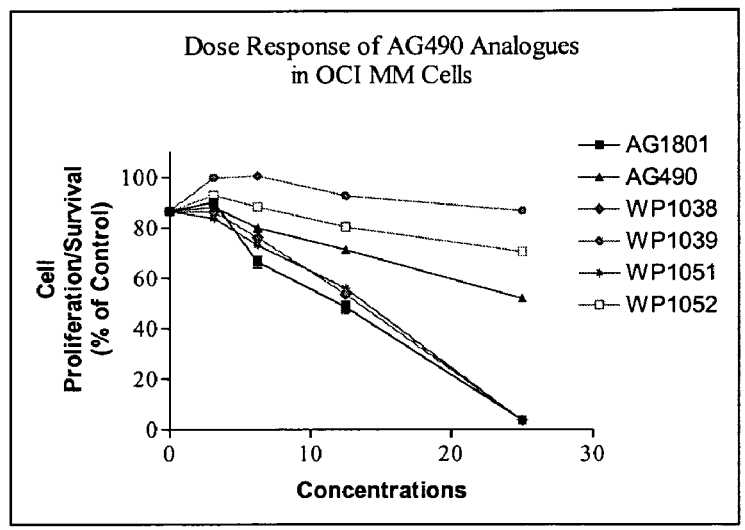
Figure 2C:
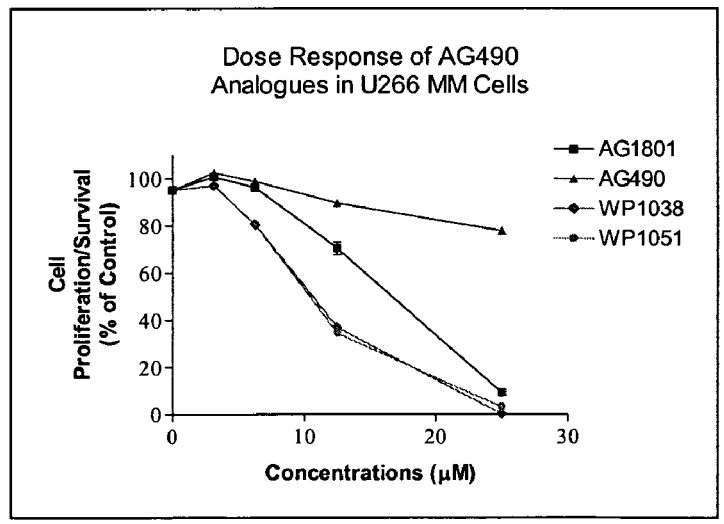

To determine the effect of AG and WP compounds on MM cell growth/survival, MM cells were incubated with the indicated concentration of AG or WP for 72 hours before cell growth and survival were estimated by MTT assay. As shown in FIGS. 2A-C, compounds active in downregulating c-myc and blocking IL-6 mediated Stat3 activation were effective in reducing the growth and survival of MM cell lines.

To determine the temporal effects and mechanism of action of AG490 and AG1801 action on c-myc expression in MM cells, MM-1 cells were incubated with 0, 25, or 50 μM of AG490 or AG1801 and harvested at 30, 60, or 120 min. Lysates were immunoblotted for c-myc or actin as a protein loading control. AG1801 rapidly reduced c-myc expression in MM-1 cells at 25 and 50 μM at all measured incubation durations. In contrast, AG490 was completely unable to affect c-myc expression at the concentrations and incubation durations tested. Semi-quantitative PCR was used to measure changes in c-myc mRNA extracted from cells treated for 30 min with AG1801 at 25 μM. GAPDH PCR was used as a control. AG1801 had minimal effects on c-myc mRNA expression when assessed by this technique.

Figure 3A:
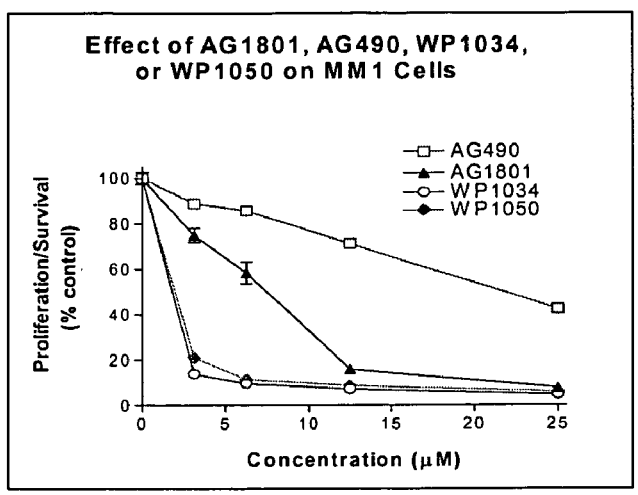
FIGS. 3A-C: Effects of AG and WP compounds on MM cell growth/survival. To determine the effect of AG and WP compounds on MM cell growth/survival, MM cells were incubated with the indicated concentration of AG or WP for 72 hours before cell growth and survival were estimated by MTT assay. Clear increases in the potency of AG1801, WP1034, and WP1050 can be observed compared to AG490.
Figure 3B:
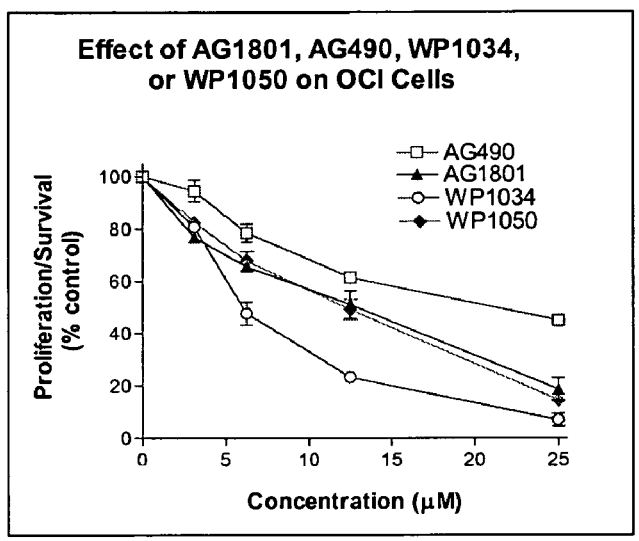
Figure 3C:
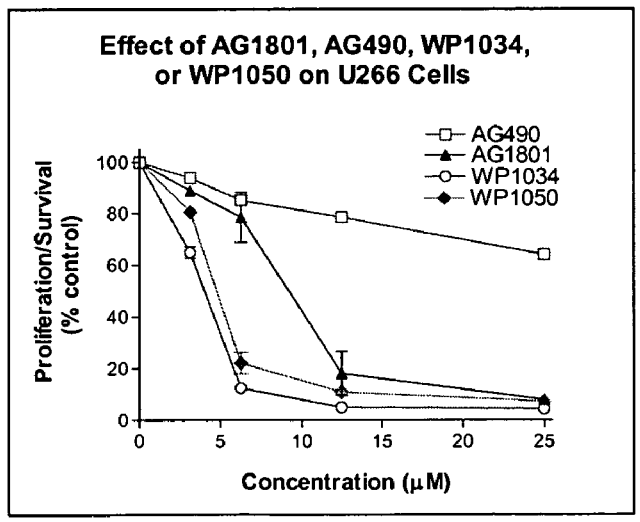

To determine the effect of AG and WP compounds on MM cell growth/survival MM cells were incubated with the indicated concentration of AG or WP for 72 hours before cell growth and survival were estimated by MTT assay. The results of this study are shown in FIGS. 3A-C.

An updated table summarizing additional data for other compounds of the present invention are included below in Table 1. The SAR for c-myc downregulation and Stat3 inhibition as well as the IC50 values for each compound are shown below in Table 1.

TABLE 1

List of Kinase Inhibitors Tyrphostins-Biological Evaluation

| V. STRUCTURE | | IC50 (μM) OCI | IC50 (μM) MM1 | IC50 (μM) U266 | C-Myc | Ⓟ-Stat 3 |
|---|---|---|---|---|---|---|
| 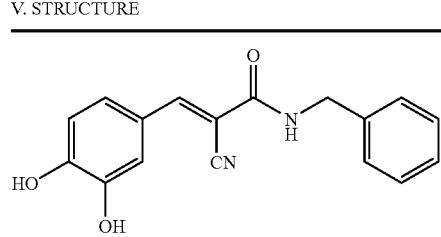 | AG 490 | >12.5 | >12.5 | >12.5 | ↓ | >25 μM ↓ |

TABLE 1-continued
List of Kinase Inhibitors Tyrphostins-Biological Evaluation
| V. STRUCTURE | | IC50 (μM) OCI | IC50 (μM) MM1 | IC50 (μM) U266 | C-Myc | (P)-Stat 3 |
|---|---|---|---|---|---|---|
| 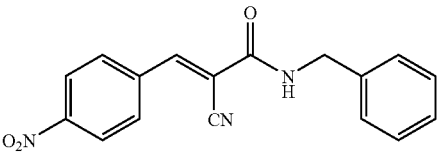 | AG 1801 | 12.0 | 7.5 | 9.0 | ↓ | ↓ |
| 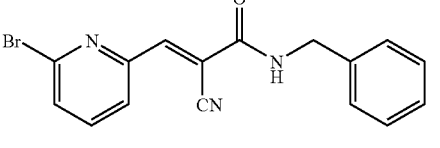 | WP 1015 | ND | 1.9 | ND | ↓ | ND |
| 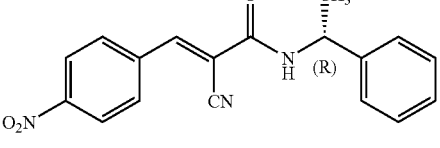 | WP 1034 | 6.3 | 3.5 | 4.5 | ↓ | ND |
| 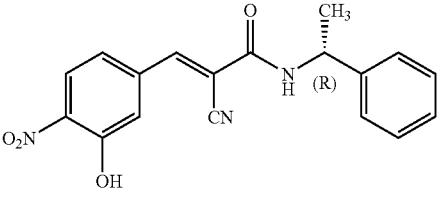 | WP 1038 | >12.5 | 6.2 | 11.8 | ↓ | ↓ |
| 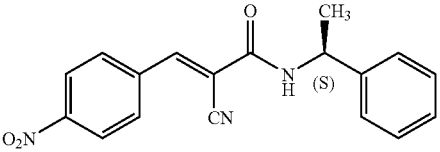 | WP 1050 | >12.5 | 2.1 | 5.0 | ↓ | ND |
| 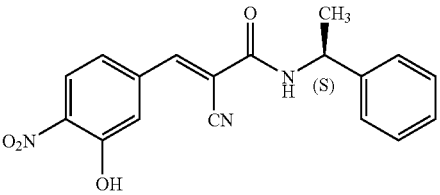 | WP 1051 | >12.5 | 5.5 | 11.1 | ↓ | ↓ |
| 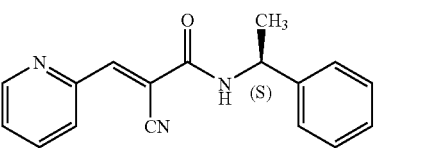 | WP 1065 | ND | 3.0 | ND | ND | ND |
| 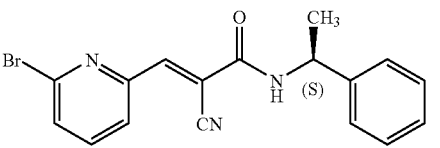 | WP 1066 | ND | 1.3 | ND | ↓ | ND |

TABLE 1-continued

List of Kinase Inhibitors Tyrphostins-Biological Evaluation

| V. STRUCTURE | | IC50 (μM) OCI | IC50 (μM) MM1 | IC50 (μM) U266 | C-Myc | ⓟ-Stat 3 |
|---|---|---|---|---|---|---|
| 2-NO2, 5-OH phenyl-CH=C(CN)-C(O)-NH-CH2-phenyl | WP 1073 | ND | >2.5 | ND | ND | ND |
| 3-NO2 phenyl-CH=C(CN)-C(O)-NH-CH2-phenyl | WP 1074 | ND | >2.5 | ND | ND | ND |
| pyridin-3-yl-CH=C(CN)-C(O)-NH-CH2-phenyl | WP 1075 | ND | >2.5 | ND | ND | ND |
| 2-NO2, 4-N(CH3)2 phenyl-CH=C(CN)-C(O)-NH-CH2-phenyl | WP 1076 | ND | >2.5 | ND | ND | ND |
| 4-Cl, 3-NO2 phenyl-CH=C(CN)-C(O)-NH-CH2-phenyl | WP 1077 | ND | 2.5 | ND | ND | ND |

SYMBOLS:
(more than) = >
(less than) = <
(not done) = ND
(inhibition) = ↓
(no effect) = —

Figure 4:
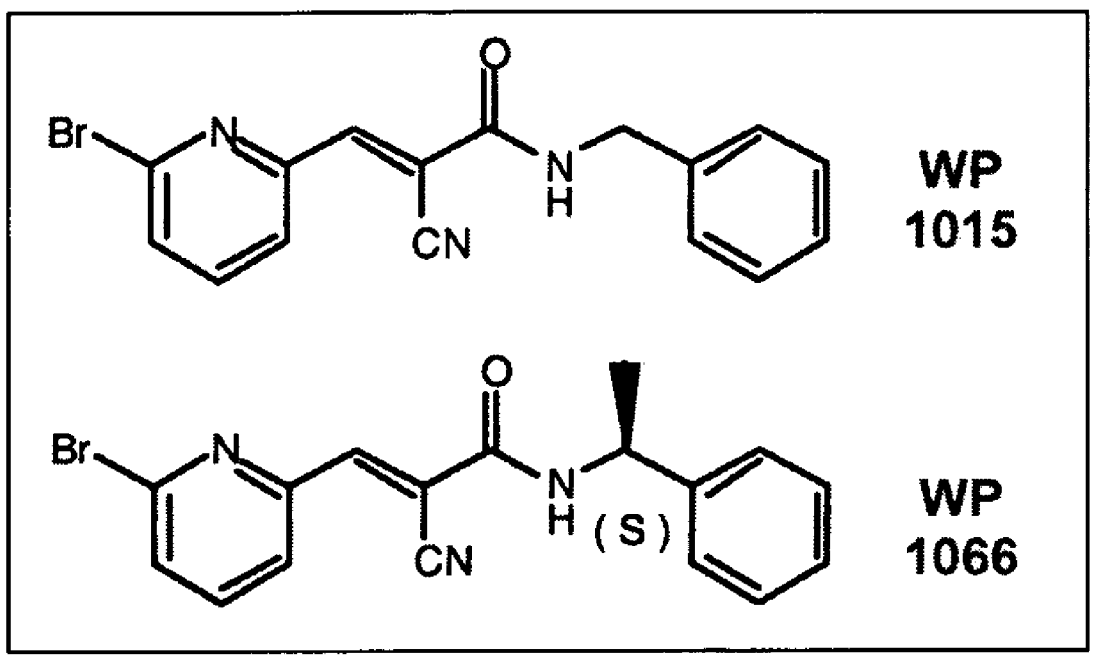
FIG. 4: Structures of WP1015 and WP1066 are shown.

Two new compounds (WP1015 and WP1066) were synthesized based on previous SAR studies, as shown in the FIG. 4. These compounds were evaluated for their signal inhibitory and anti-proliferative/apoptotic properties on multiple myeloma, lymphoma and chronic myelogenous leukemia cell lines. WP1015, WP1034, AG1801, and AG490 were tested across a range of concentrations (6, 12, and 25 μM) for their ability to inhibit c-myc expression using immunoblots. WP1015 was more active than previously synthesized WP compounds in inhibiting c-myc protein expression. AG490 had little or no effect on c-myc expression at concentrations up to 50 μM. Similarly, WP1015 was more effective in inhibiting Stat3 phosphorylation in MM-1 cells than previous compounds.

WP1066 was then synthesized; the additional modification in WP1066 (compared to WP1015) resulted in improved activity. As shown using immunoblots, WP1066 was more active in suppressing c-myc protein expression than WP1015. These immunoblots tested a range of concentrations (1.56-25 μM for WP compounds) and used β-actin as a control. Cells were also treated for 0-30 min. with the potent translation inhibitor, cycloheximide (CHX) to determine whether WP1066 mediates similar effects on c-myc protein expression. CHX at much higher concentrations did not result in the rapid reduction of c-myc as seen in WP1066 treated cells, suggesting possible effects on both translation and/or degradation of c-myc by WP11066.

Additional cell types were examined for response to treatment with WP1066. As shown using immunoblots, WP1066 caused rapid downregulation of c-myc protein in LP non-Hodgkin' lymphoma cells as well as MM cells, demonstrating c-myc down-regulatory activity is not restricted to multiple myeloma cells alone. Multiple incubation periods for WP1066 (5, 15, 30, 60 min.) were tested; a strong reduction in c-myc was observed at the shortest (5 min.) incubation period.

Further studies were conducted to determine the dose and time dependent effects of these new compounds on IL-6 mediated Stat3 activation, c-myc protein expression and antiproliferative of LP and other cell types. As shown in using immunoblots with a range (3-25 µM of WP compounds), both WP1066 and WP1015 blocked IL-6 mediated Stat3 activation and reduced c-myc expression in LP cells. WP1066 had slightly better activity than WP1015, demonstrating coincident improvement of compound action on multiple cell types.

Figure 5:
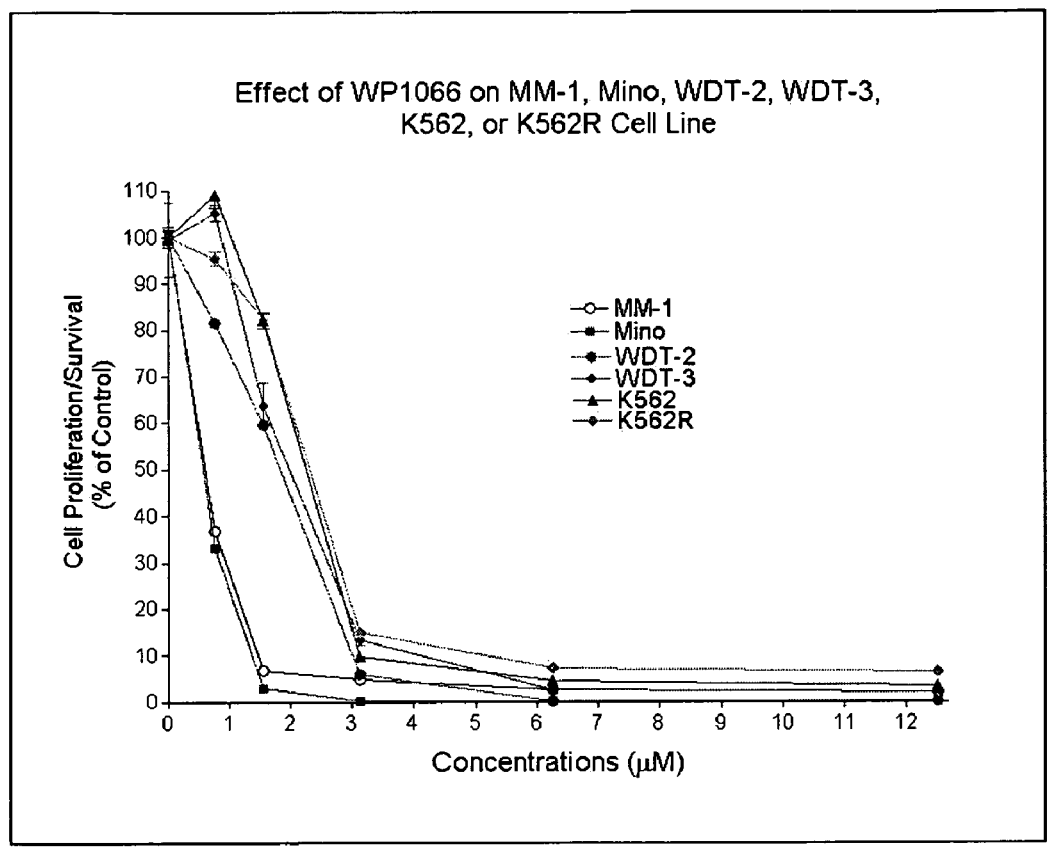
FIG. 5: Effect of WP1066 on multiple cancer cell lines. WP1066 was effective in reducing cell proliferation in multiple cell lines, demonstrating a potent anti-cancer effect.

The anti-proliferative/apoptotic actions of WP1066 were also examined on cell lines known to overexpress c-myc. As shown in FIG. 5, WP1066 treatment induced dose-dependent anti-tumor effects on multiple myeloma (MM-1), mantle cell lymphoma (Mino) and CML (WDT-2, WDT-3, K562, K562-R) cells lines, including those resistant to the kinase inhibitor Imatinib mesylate (K562-R). Thus WP1066 clearly exerts a potent inhibition of cell proliferation and/or survival in multiple cancer cell lines, and WP1066 will be used as a therapeutic.

All of the compositions disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 4

Compounds Display Potent Anti-Cancer Effects In Vivo

Figure 6:
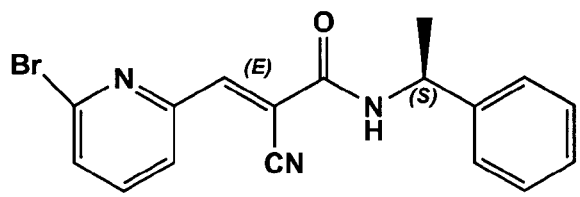
FIG. 6: Structures of WP1066, WP1130, and WP1129 are shown. $IC_{50}$ values for these compounds against MM-1 myeloma tumors are shown. This figure illustrates the improved activity of these compounds.
Figure 6:
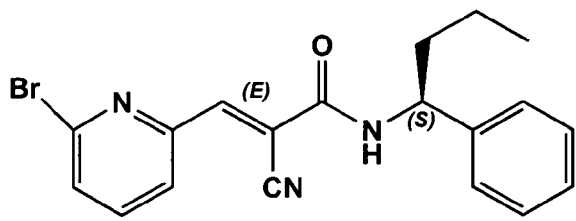
Figure 6:
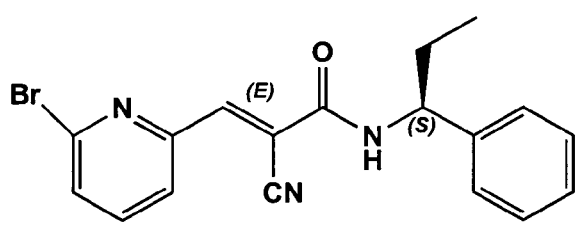

Compounds WP1129 and WP1130 were synthesized via the method described in Example 1. The structures of WP1129 and WP1130 are shown in FIG. 6. $IC_{50}$ values for these compounds against MM-1 myeloma tumors are also shown in FIG. 6, and these compounds display $IC_{50}$ values even better than compound WP1066. The increased potency of WP1129 and WP1130 support the use of these compounds to treat cell proliferative diseases such as cancer.

Figure 7:
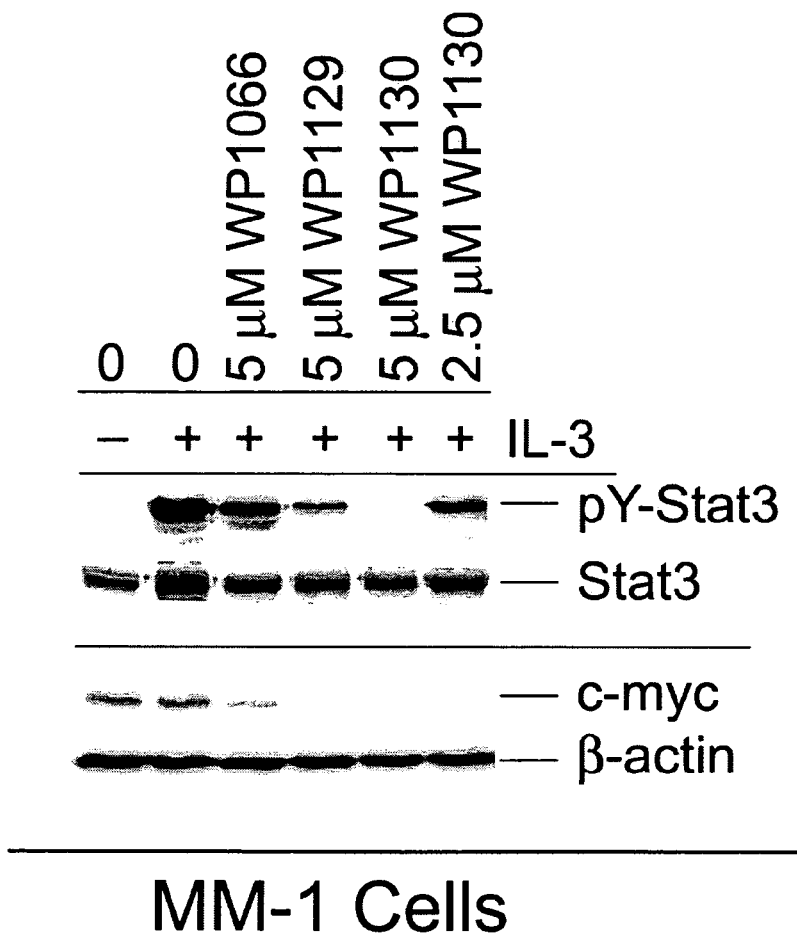
FIG. 7: Improved c-myc/Stat3 inhibition with WP1066, WP1130, and WP1129. The compounds were compared with regard to their Stat3/c-myc inhibitory activity in MM-1 cells. Strong inhibition of c-myc/Stat3 was observed for WP1066, WP1130, and WP1129.

An improved inhibition of c-myc/Stat3 by WP1066, WP1130, and WP1129 was observed (FIG. 7). The compounds were compared with regard to their Stat3/c-myc inhibitory activity in MM-1 cells. Strong inhibition of c-myc/Stat3 was observed for WP1066, WP1130, and WP1129.

Figure 8:
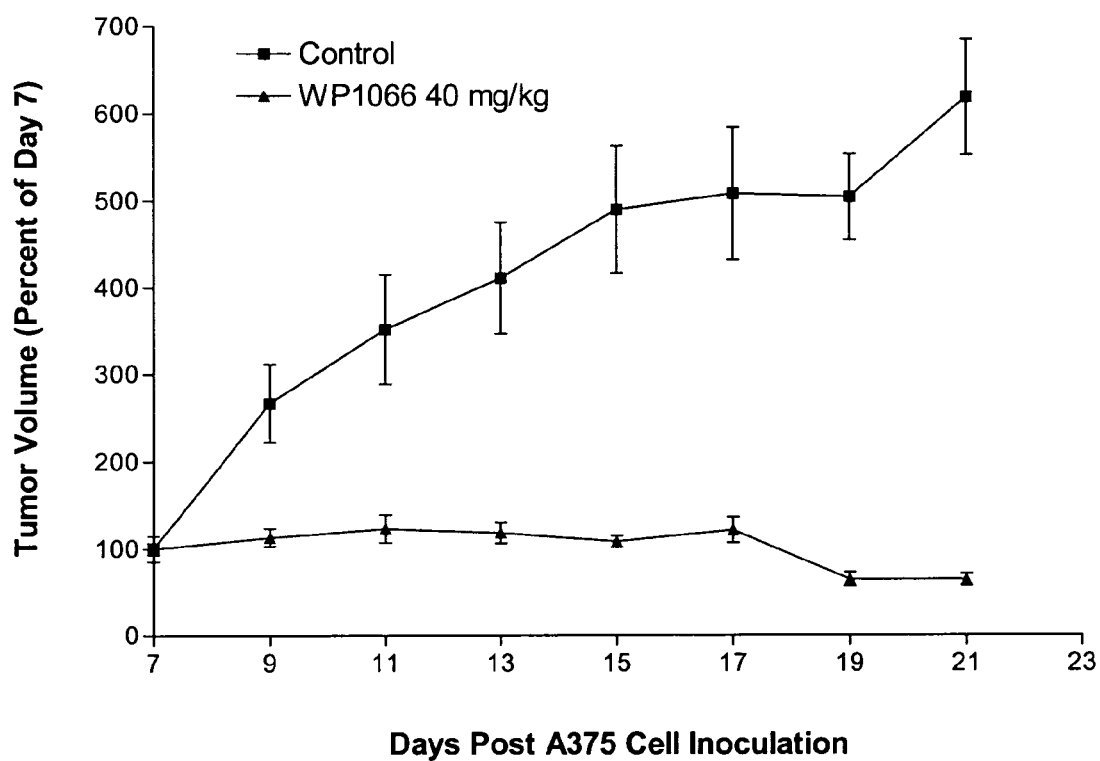
FIG. 8: WP1066 decreases tumor size in vivo. The results of animal studies of human A375 melanoma tumors growing in nude mice, treated with WP1066 after tumors reached a palpable size, are shown. Animals received 40 mg/kg WP1066 every other day (QID) for a total of 8 injections. The experiment was stopped on day 21 when the control group reached maximum tumor burden. These results indicate that WP1066 reduces tumor volume in vivo.
Figure 9:
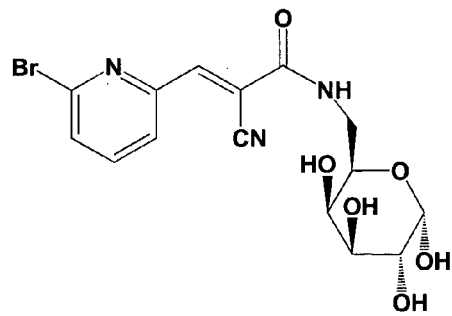
FIG. 9: The structures of WP1119, WP1026, and WP1127 are shown. Examples of the kinds of monosaccharides (e.g., galactose) and monosaccharide derivatives (e.g., an acetylated monosaccharide such as acetylated galactose, 1,2,3,4-diisopropylideno-D-galactose) that can be incorporated into the structures of compounds of the present invention are exemplified by the structures of WP1119, WP1026, and WP1127.
Figure 9:
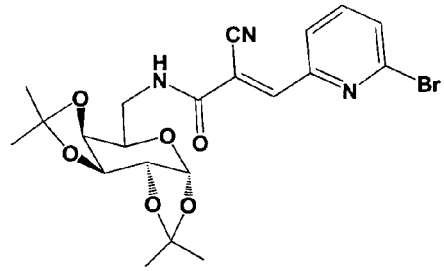
Figure 9:
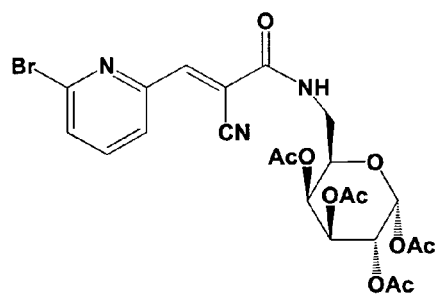

WP1066 was found to decrease tumor size in vivo. The results of animal studies of human A375 melanoma tumors growing in nude mice, treated with WP1066 after tumors reached a palpable size, are shown in FIG. 8. The following animal model was used to evaluate the anti-tumor and anti-cancer effects of the compounds: on Day 0, A375 cells were suspended to 20×106 cells/ml in RPMI 1640 medium. On day 0, 0.2 ml of this suspension containing A375 cells was injected (s.c.) into female Swiss nude mice 6-7 weeks of age. On Day 7, 40 mg/kg of WP1066 was injected (i.p.) into the above mice in a 0.1 ml suspension of DMSO/PEG300 (50/50) on a qd, every other day schedule for 8 injections. Five mice per experimental group were used, including a vehicle (DMSO/PEG300) control group. Animals received 40 mg/kg WP1066 every other day (QID) for a total of 8 injections. The control group reached maximum tumor burden at day 21, and for this reason the experiment was stopped. WP1066 displayed strong anti-cancer and anti-tumor effects in vivo. These results indicate that WP1066, and other compounds described herein, may be used to treat hyperproliferative diseases such as cancer.

REFERENCES

The following references, to the extent that they provide exemplary procedural or other details supplementary to those set forth herein, are specifically incorporated herein by reference.

U.S. Pat. No. 6,596,828B2
U.S. Pat. No. 6,433,018
U.S. Pat. No. 6,420,338
U.S. Application 2003/0013748
Alas and Bonavida, *Clin. Cancer Res.*, 9(1):316-26, 2003.
Arbel et al., *Am. J. Obstet. Gynecol.*, 188(5):1283-90, 2003.
Bharti et al., *J. Immunol.*, 171(7):3863-3871, 2003.
Burdelya et al., *Mol. Cancer Ther.*, 1(11):893-9, 2002.
Catlett-Falcone et al., *Immunity*, 10(1): 105-15, 1999.
Constantin et al., *Eur. J. Immunol.*, 28(11):3523-9, 1998.
Hallek et al., *Blood*, 91(1):3-21, 1998.
Hideshima et al., *J. Biol. Chem.*, 277(19):16639-47, 2002.
Jernberg-Wiklund et al., *Int. J. Cancer*, 51(1):116-23, 1992.
Kerr et al., *FEBS Lett.*, 546(1):1-5, 2003.
Kuehl et al., *Curr. Top Microbiol. Immunol.*, 224:277-82, 1997.
Meydan et al., *Nature*, 379(6566):645-8, 1996.
"Remington's Pharmaceutical Sciences" 15th Edition, pages 1035-1038 and 1570-1580.
Selvanayagam et al., *Blood*, 71(1):30-5, 1988.
Verma et al., *Cancer Metastasis Rev.*, 22(4):423-34, 2003.

What is claimed is:

1. A compound comprising the chemical formula:

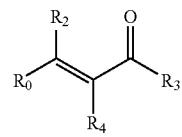

wherein $R_0$ is chosen from the group consisting of:

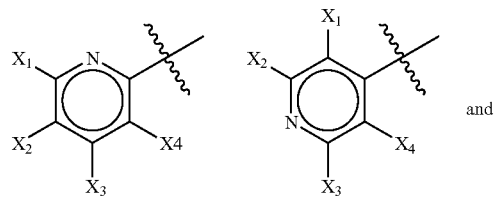

and

-continued

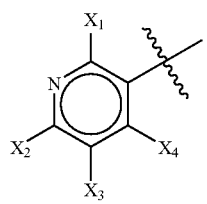

where $X_1$, $X_2$, $X_3$, and $X_4$, are each independently selected from the group consisting of hydrogen, halogen, OH, and $NO_2$;

$R_2$ is selected from the group consisting of alkyl, alkenyl, alkynyl, alkoxy, alkylaryl, halogen, hydrogen, OH, $NO_2$, thioether, amine, SH, and $NH_2$;

$R_3$ is

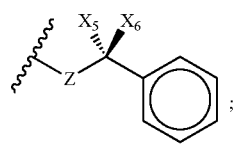

where $R_4$ is CN;
where Z is NH, and
where $X_5$ and $X_6$ are each independently chosen from the group consisting of hydrogen and lower alkyl.

2. The compound of claim 1, wherein $R_2$ is hydrogen.
3. The compound of claim 1, wherein $R_0$ is:

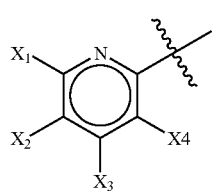

4. The compound of claim 3, wherein $X_1$ is a halogen.
5. The compound of claim 4, wherein $X_1$ is Br.
6. The compound of claim 1, wherein $X_1$, $X_2$, $X_3$, and $X_4$ are hydrogen.
7. The compound of claim 1, wherein $X_6$ is a lower alkyl.
8. The compound of claim 1, having the formula:

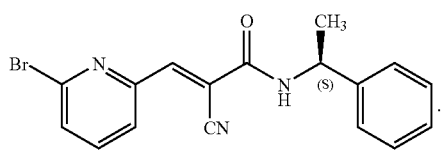

9. The compound of claim 1, having the formula:

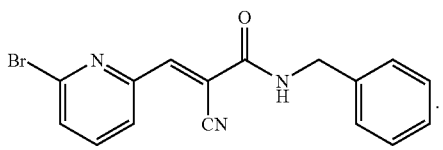

10. The compound of claim 1, having the formula:

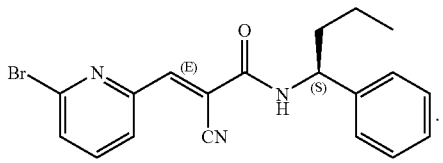

11. The compound of claim 1, having the formula:

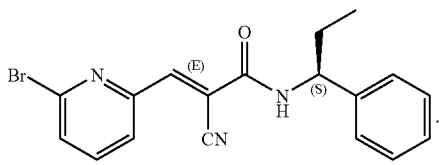

12. The compound of claim 1, having the formula:

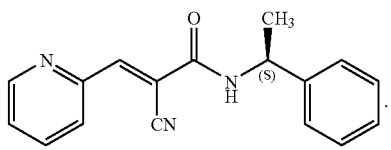

13. The compound of claim 1, having the formula:

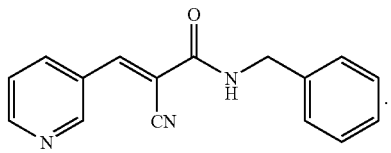

14. A method of treating atherosclerosis, pulmonary fibrosis, myelofibrosis, chronic myeloid, leukemia, myeloma tumors, squamous cell carcinoma, keratinocyte proliferation or psoriasis, comprising administering a therapeutically relevant amount of a first compound to a subject; wherein the amount of the first compound is effective to treat atherosclerosis, pulmonary fibrosis, myelofibrosis, chronic myeloid, leukemia, myeloma tumors, squamous cell carcinoma, keratinocyte proliferation or psoriasis; and wherein the first compound has the chemical formula:

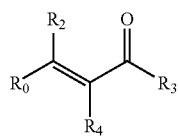

wherein $R_0$ is chosen from the group consisting of:

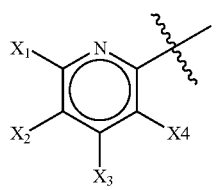 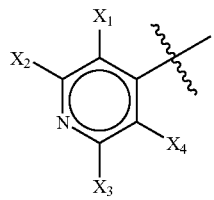 and

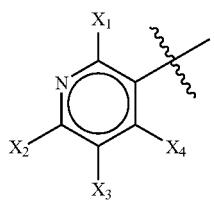

where $X_1$, $X_2$, $X_3$, and $X_4$, are each independently selected from the group consisting of hydrogen, halogen, OH, and $NO_2$;

$R_2$ is selected from the group consisting of alkyl, alkenyl, alkynyl, alkoxy, alkylaryl, halogen, hydrogen, OH, $NO_2$, thioether, amine, SH, and $NH_2$;

$R_3$ is

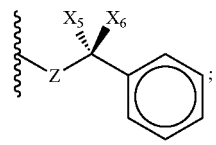

where $R_4$ is CN;
where Z is NH, and
where $X_5$ and $X_6$ are each independently chosen from the group consisting of hydrogen and lower alkyl.

15. The method of claim 14, wherein the subject is a mammal.

16. The method of claim 15, wherein the mammal is a human.

17. The method of claim 14, wherein the first compound is comprised in a pharmaceutically acceptable excipient, diluent, or vehicle.

18. The method of claim 14, wherein stat3 activation is reduced in a cell of the subject.

19. The method of claim 14, wherein c-myc expression is reduced in a cell of the subject.

20. The method of claim 14, wherein the first compound is administered in combination with a therapeutically relevant amount of a second compound.

21. The method of claim 20, wherein the second compound is an anti-cancer compound.

22. The method of claim 14, wherein the first compound is administered in combination with a surgery, a radiation therapy, or a gene therapy.

23. The compound of claim 1, wherein $X_5$ and $X_6$ are both hydrogen.

* * * * *

UNITED STATES PATENT AND TRADEMARK OFFICE
CERTIFICATE OF CORRECTION

PATENT NO. : 7,745,468 B2  Page 1 of 1
APPLICATION NO. : 11/010834
DATED : June 29, 2010
INVENTOR(S) : Waldemar Priebe et al.

It is certified that error appears in the above-identified patent and that said Letters Patent is hereby corrected as shown below:

In title page, item (73) Assignee, delete "Systems" and insert --System-- therefor.

In claim 1, column 32, line 64, in chemical drawing, delete "X4" and insert --$X_4$-- therefor.

In claim 3, column 33, line 46, in chemical drawing, delete "X4" and insert --$X_4$-- therefor.

In claim 14, column 35, line 18, in chemical drawing, delete "X4" and insert --$X_4$-- therefor.

Signed and Sealed this

Fifth Day of October, 2010

David J. Kappos
*Director of the United States Patent and Trademark Office*